US012741936B2

(12) United States Patent
Uehira

(10) Patent No.: US 12,741,936 B2
(45) Date of Patent: Sep. 22, 2026

(54) COMPOUND, POLYMERIZABLE COMPOSITION, POLYMER, AND POLYMERIZED FILM

(71) Applicant: FUJIFILM Corporation, Tokyo (JP)

(72) Inventor: Shigeki Uehira, Shigara (JP)

(73) Assignee: FUJIFILM Corporation, Tokyo (JP)

( * ) Notice: Subject to any disclaimer, the term of this patent is extended or adjusted under 35 U.S.C. 154(b) by 484 days.

(21) Appl. No.: 18/502,597

(22) Filed: Nov. 6, 2023

(65) Prior Publication Data

US 2024/0092733 A1 Mar. 21, 2024

Related U.S. Application Data

(63) Continuation of application No. PCT/JP2022/024583, filed on Jun. 20, 2022.

(30) Foreign Application Priority Data

Jun. 24, 2021 (JP) ................................ 2021-105117

(51) Int. Cl.
*C08F 12/32* (2006.01)
*C07C 311/21* (2006.01)

(52) U.S. Cl.
CPC ............ *C07C 311/21* (2013.01); *C08F 12/32* (2013.01)

(58) Field of Classification Search
CPC ...... C07C 311/21; C07C 311/00; C08F 12/30; C08F 12/32
See application file for complete search history.

(56) References Cited

U.S. PATENT DOCUMENTS 10,087,263 B2 10/2018 Kodama et al.
2013/0026047 A1 1/2013 Komatsu et al.
(Continued)

FOREIGN PATENT DOCUMENTS

CN 103459436 A 12/2013
CN 105492508 A 4/2016
(Continued)

OTHER PUBLICATIONS

International Search Report dated Aug. 23, 2022, issued in International Application No. PCT/JP2022/024583.
(Continued)

*Primary Examiner* — Mark S Kaucher
(74) *Attorney, Agent, or Firm* — Sughrue Mion, PLLC

(57) ABSTRACT

Provided are a compound represented by the following general formula (I), a polymerizable composition including the compound, a polymer including a constituent component derived from the compound, and a polymerized film, General formula (I)

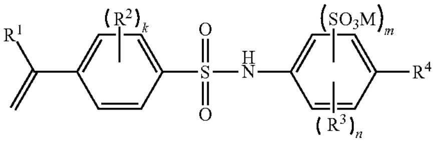

in Formula (I), $R^1$ represents a hydrogen atom or a lower alkyl group, $R^2$ represents a group such as an alkenyl group, $R^3$ and $R^4$ represent groups such as alkenyl groups, or groups that are combinations of an alkyl group, an alkenyl group, an aryl group, an oxygen atom, a $—SO_3^-M^+$ group, or an arylsulfonylamino (Continued)

group, $M^+$ represents $H^+$ or the like, k is an integer of 0 to 4, n is an integer of 0 to 4, m is an integer of 0 to 4, with the proviso that n and m satisfy $1 \leq n+m \leq 4$, and when m is 0, at least one of $R^3$ is a group having a $—SO_3^-M^+$ group.

9 Claims, 4 Drawing Sheets

(56) References Cited

U.S. PATENT DOCUMENTS

| | | | | |
|---|---|---|---|---|
| 2014/0011129 | A1* | 1/2014 | Murai | C07C 311/21<br>430/108.22 |
| 2016/0177006 | A1 | 6/2016 | Sano et al. | |
| 2017/0152331 | A1 | 6/2017 | Iizuka et al. | |

FOREIGN PATENT DOCUMENTS

| | | | |
|---|---|---|---|
| CN | 106103503 | A | 11/2016 |
| JP | 48-102833 | A | 12/1973 |
| JP | 2012-214797 | A | 11/2012 |
| JP | 2013-49259 | A | 3/2013 |
| JP | 2014-195798 | A | 10/2014 |
| WO | 2012/133871 | A1 | 10/2012 |

OTHER PUBLICATIONS

Written Opinion dated Aug. 23, 2022, issued in International Application No. PCT/JP2022/024583.

International Preliminary Report on Patentability (with translation of Written Opinion) dated Dec. 14, 2023, issued in International Application No. PCT/JP2022/024583.

* cited by examiner

COMPOUND, POLYMERIZABLE COMPOSITION, POLYMER, AND POLYMERIZED FILM

CROSS-REFERENCE TO RELATED APPLICATIONS

This application is a Continuation of PCT International Application No. PCT/JP2022/024583 filed on Jun. 20, 2022, which claims priority under 35 U.S.C. § 119 (a) to Japanese Patent Application No. 2021-105117 filed in Japan on Jun. 24, 2021. Each of the above applications is hereby expressly incorporated by reference, in its entirety, into the present application.

BACKGROUND OF THE INVENTION

1. Field of the Invention

The present invention relates to a compound, a polymerizable composition including the compound, a polymer of the compound, and a polymerized film including the polymer.

2. Description of the Related Art

Functional polymers and the like are used in various technical fields such as polymer functional films such as ion exchange films, reverse osmosis films, forward osmosis films, and gas separation films, and electrochemical devices. In order to use functional polymers, research and development of polymers capable of exhibiting characteristics required for the usage and functions of individual products and monomers and the like forming such polymers have been in demand, and polymers, monomers, and the like having various chemical structures have already been studied.

For example, JP2013-049259A describes, as a polymerizable compound for forming an intermediate layer disposed between a support and a photosensitive layer in lithographic printing plates, for example, a compound in which the phenyl group of styrene and the phenyl group of benzenesulfonic acid are bonded to each other via a sulfonamide bond so that the sulfonic group is at the para position. Further, JP2012-214797A describes, as a polymerizable monomer for constituting a charge control agent used in a developer carrying member equipped in an image forming apparatus, a styrene compound having a salicylic acid unit incorporated therein, more specifically, a polymerizable compound in which the phenyl group of styrene and salicylic acid are bonded to each other via a sulfonamide bond so that the phenolic hydroxy group is at the para position. Further, JP1973-102833A (JP-548-102833A) describes, as a water-soluble dye, a compound (reactive organic dye) in which an α-bromostyrene skeleton and a residue of a water-soluble organic dye such as anthraquinone are bonded to each other via a group including a sulfonamide bond.

SUMMARY OF THE INVENTION

In recent years, polymer functional films and electrochemical devices have come to be, for example, applied in broader applications and used in more various forms, and are expected to be used in acidic environments or alkaline environments; thus, functional polymers are exposed in such environments in some cases. For this reason, for functional polymers and further for monomers forming functional polymers, at least one of acid resistance or alkali resistance has come to be in demand.

However, for existing functional polymers, in particular, the polymers and monomers described in JP2013-049259A, JP2012-214797A, and JP1973-102833A (JP-S48-102833A), the exhibition of or improvement in acid resistance and alkali resistance has not been studied at all.

An object of the present invention is to provide a compound exhibiting alkali resistance and a polymerizable composition including the compound. Another object of the present invention is to provide a polymer including a constituent component derived from the above-described compound and exhibiting acid resistance and alkali resistance, and a polymerized film including the polymer and exhibiting acid resistance and alkali resistance.

The inventor of the present invention has found that, in the case of using, as a monomer for forming a polymer, a compound having a chemical structure in which a sulfonic group-containing benzene ring is introduced, into the para position of the benzene ring of a styrene compound, with a sulfonamide bond disposed therebetween, the monomer exhibits acid resistance. As a result of further studies, the inventor has found that homopolymerization or copolymerization of this monomer provides a polymer that exhibits acid resistance and alkali resistance. The present invention has been accomplished on the basis of such findings.

Specifically, the above-described objects of the present invention have been addressed by the following means.

<1> A compound represented by a general formula (I) below:

General formula (I)

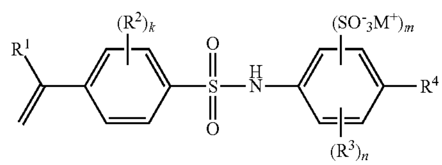

in the general formula (I), $R^1$ represents a hydrogen atom or a lower alkyl group, $R^2$ represents an alkyl group, an alkenyl group, an aryl group, a halogen atom, a hydroxy group, or an amino group, $R^3$ represents an alkyl group, an alkenyl group, an aryl group, a halogen atom, an amino group, a carboxy group, or a group having a $—SO_3^-M^+$ group, or a group that is a combination of an alkyl group, an alkenyl group, an aryl group, an oxygen atom, a $—SO_3^-M^+$ group, or an arylsulfonylamino group, $R^4$ represents a hydrogen atom, an alkyl group, an alkenyl group, an aryl group, a halogen atom, an amino group, or a carboxy group, or a group that is a combination of an alkyl group, an alkenyl group, an aryl group, an oxygen atom, a $—SO_3^-M^+$ group, or an arylsulfonylamino group, $M^+$ represents $H^+$, $Li^+$, $Na^+$, $K^+$, $Cs^+$, or an ammonium salt, k is an integer of 0 to 4, and when k is an integer of 2 or more, a plurality of $R^2$'s may be the same or different, and may be linked together to form a ring, n is an integer of 0 to 4, and when n is an integer of 2 or more, a plurality of $R^3$'s may be the same or different, and may be linked together to form a ring, m is an integer of 0 to 4, and when m is an integer of 2 or more, a plurality of $-SO_3^-M^+$ groups may be the same or different, with the proviso that n and m satisfy $1 \leq n+m \leq 4$, and when m is 0, at least one of $R^3$ is a group having a $-SO_3^-M^+$ group.

<2> The compound according to <1>, wherein the compound represented by the general formula (I) is represented by a general formula (II) below:

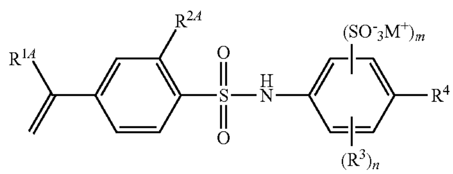

in the general formula (II), $R^{1A}$ represents a hydrogen atom or a methyl group, $R^{2A}$ represents a hydrogen atom, $-CH{=}CH_2$, or $-C(CH_3){=}CH_2$, $R^3$, $R^4$, and $M^+$ have the same meanings as $R^3$, $R^4$, and $M^+$ of the general formula (I), m is 1 or 2, and n is an integer of 0 to 2.

<3> The compound according to <1>, wherein the compound represented by the general formula (I) is represented by a general formula (III) below:

General formula (III)

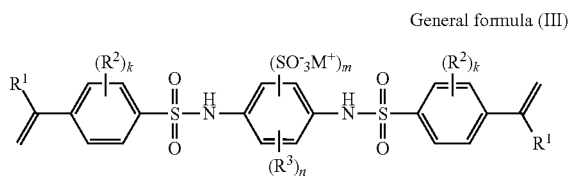

in the general formula (III), $R^1$ to $R^3$, $M^+$, k, m, and n have the same meanings as $R^1$ to $R^3$, $M^+$, k, m, and n in the general formula (I).

<4> The compound according to <2>, wherein the compound represented by the general formula (II) is represented by a general formula (IV) below:

General formula (IV)

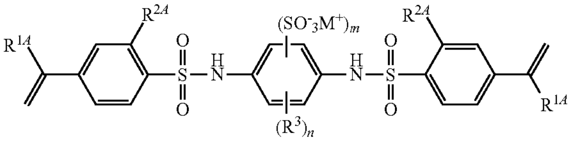

in the general formula (IV), $R^{1A}$, $R^{2A}$, $R^3$, $M^+$, m, and n have the same meanings as the $R^{1A}$, $R^{2A}$, $R^3$, $M^+$, m, and n of the general formula (II).

<5> The compound according to <1>, wherein the compound represented by the general formula (I) is represented by a general formula (V) below:

General formula (V)

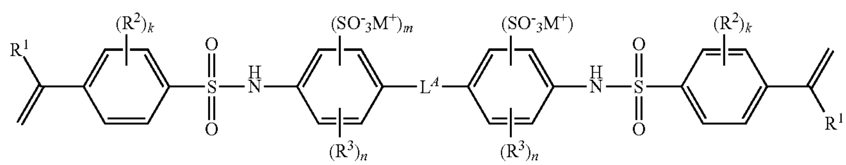

in the general formula (V), $R^1$ to $R^3$, $M^+$, k, m, and n have the same meanings as $R^1$ to $R^3$, $M^+$, k, m, and n in the general formula (I), and $L^A$ represents a single bond or a divalent linking group.

<6> The compound according to <2>, wherein the compound represented by the general formula (II) is represented by a general formula (VI) below:

General formula (VI)

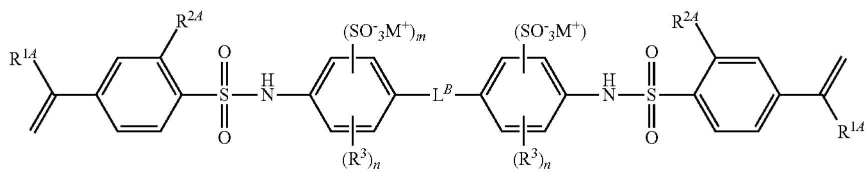

in the general formula (VI), $R^{1A}$, $R^{2A}$, $R^3$, $M^+$, m, and n have the same meanings as the $R^{1A}$, $R^{2A}$, $R^3$, $M^+$, m, and n of the general formula (II), and $L^B$ represents a single bond, $-CH{=}CH-$, or an oxygen atom.

<7> A polymerizable composition including the compound according to any one of <1> to <6> above.

<8> A polymer including a constituent component derived from the compound according to any one of <1> to <6> above.

<9> A polymerized film including the polymer according to <8> above.

The present invention can provide a compound exhibiting alkali resistance and a polymerizable composition including the compound. Further, the present invention can provide a polymer including a constituent component derived from the above-described compound and exhibiting acid resistance and alkali resistance, and a polymerized film including the polymer and exhibiting acid resistance and alkali resistance.

The above and other features and advantages according to the present invention will become more apparent from the following description, with reference where appropriate to the accompanying drawings.

DESCRIPTION OF THE PREFERRED EMBODIMENTS

Figure 1:
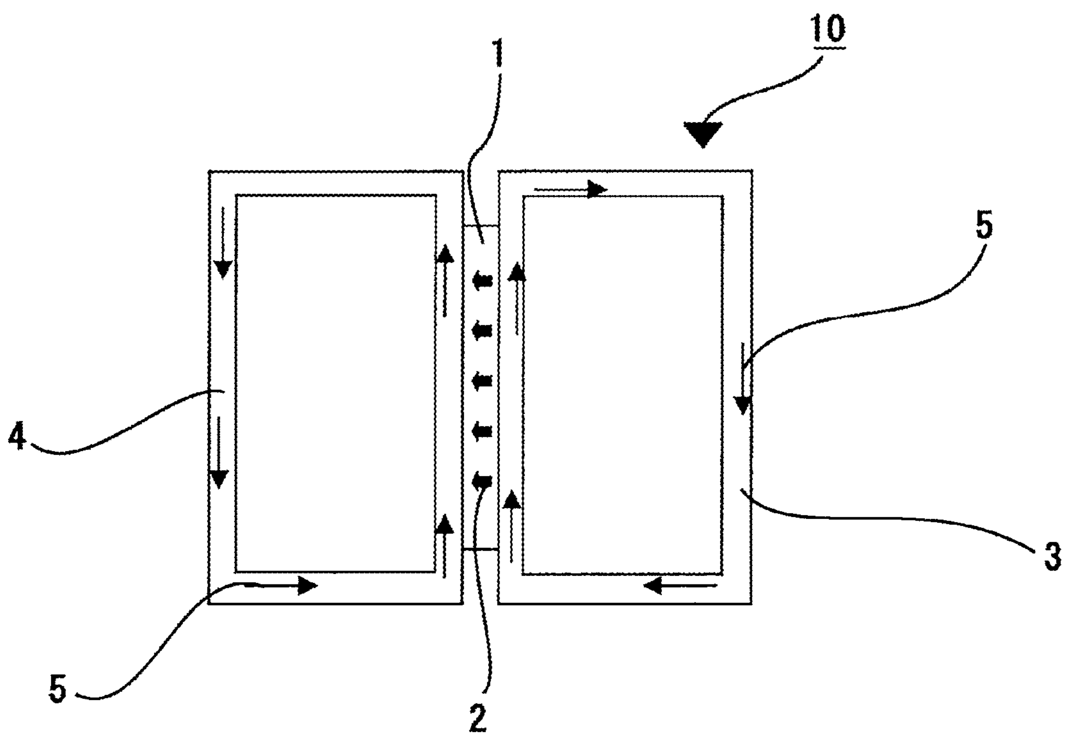
FIG. 1 is a schematic view of a flow path of an apparatus for measuring the water permeability of a polymerized film.

In the present invention, numerical ranges described in the form of "a value 'to' a value" mean ranges including the values as a lower limit value and an upper limit value. Note that, in the present invention, when a plurality of numerical ranges are set in a stepwise manner to describe the content, a property, or the like of a component, the upper limit values and the lower limit values forming the numerical ranges are not limited to the specific combinations described before and after "to" and forming the specific numerical ranges, and the numerical values of the upper limit values and the lower limit values forming numerical ranges can be appropriately combined. The term "dissociable group" refers to a group that can be reversibly decomposed into its component atoms, ions, atomic groups, or the like.

In the present invention, the term compound (for example, when something is referred to as something compound) is used in the meaning that includes not only the compound itself but also a salt thereof and an ion thereof. In addition, the term is used in the meaning that includes derivatives in which a portion is changed, for example, a substituent is introduced as long as advantages according to the present invention are not impaired.

In the present invention, the description of "(meth)acryl" or the like means $—C(═O)CH═CH_2$ and $—C(═O)C(CH_3)═CH_2$, or at least one of $—C(═O)CH═CH_2$ or $—C(═O)C(CH_3)═CH_2$; "(meth)acrylamide" means acrylamide and methacrylamide, or at least one of acrylamide or methacrylamide; "(meth)acrylate" means acrylate and methacrylate, or at least one of acrylate or methacrylate.

In addition, in the general formulas, unless otherwise specified, in the case where there are a plurality of groups denoted by the same symbol, these may be the same or different; similarly, in the case where there are repeats of a plurality of partial structures, these repeats mean both repeats of the same kind and a mixture of repeats of kinds different within the defined range.

Furthermore, in the general formulas, for geometric isomers, which are the substitution forms of a double bond, even when one of the isomers is described for convenience of indication, such a general formula may mean an E isomer, a Z isomer, or a mixture thereof unless otherwise specified. Further, when compounds represented by the general formulas have an ethylenic double bond as a linking group or the like, the ethylenic double bond may be polymerized in the polymer of such a compound.

In the present invention, substituents, linking groups, and the like (hereafter, referred to as substituents etc.) for which substituted or unsubstituted is not clearly specified means that such a group may have an appropriate substituent. Thus, in the present invention, even in the case of a simple description as a YYY group, this YYY group encompasses the form not having substituents and further the forms having substituents. This also applies to compounds for which substituted or unsubstituted is not clearly specified.

In the present invention, unless otherwise specified, when a plurality of substituents etc. are adjacent to each other, they may be linked together or fused to form a ring.

Compound Represented by General Formula (I)

A compound according to the present invention is a polymerizable compound having a chemical structure in which a sulfonic group-containing benzene ring is introduced into the para position of the benzene ring of a styrene compound, with a sulfonamide bond disposed therebetween, and can be referred to as a styrene sulfonamide compound. Such a compound according to the present invention is specifically represented by a general formula (I) below. This compound exhibits high alkali resistance and further exhibits its water solubility.

In the present invention, the term "alkali resistance" refers to a property in which a compound, a polymer, a polymerized film, or the like is less likely to undergo a hydrolysis reaction in an alkaline environment (a property in which decomposition can be suppressed). Partial decomposition of such compounds and the like cannot be avoided due to the strength of alkalinity, the prolonged period of exposure to an alkaline environment, or the like; however, for the present invention, at least Examples described later have passed the test.

The acid resistance refers to a property in which a polymer, a polymerized film, or the like is less likely to undergo a hydrolysis reaction in an acidic environment (a property in which decomposition can be suppressed). Partial decomposition of such polymers and the like cannot be avoided due to the strength of the acidity, the prolonged period of exposure to an acidic environment, or the like; however, for the present invention, at least Examples described later have passed the test. Note that, for such a compound according to the present invention, styrene (ethylenic double bond) is easily polymerized under an acidic environment, but the other chemical moieties exhibit acid resistance.

As will be described later, a compound exhibiting the above-described properties according to the present invention can be homopolymerized or copolymerized to thereby form a polymer exhibiting high acid resistance and high alkali resistance by utilizing the above-described properties of the compound. Therefore, a compound according to the present invention can be used in a wide range of applications, and is particularly suitable as a compound for a polymer constituting a polymerized film.

General formula (I)

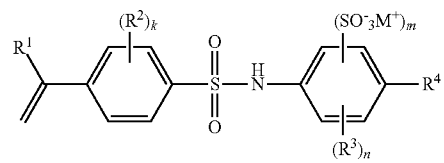

In the general formula (I), $R^1$ represents a hydrogen atom or a lower alkyl group.

The lower alkyl group that can be represented by $R^1$ is an alkyl group having 1 to 4 carbon atoms, and preferably an alkyl group having 1 to 3 carbon atoms. The lower alkyl group may be linear, branched, or cyclic. Examples of the lower alkyl group include methyl, ethyl, n-propyl, iso-propyl, n-butyl, and tert-butyl.

$R^1$ is preferably a hydrogen atom or a methyl group, and more preferably a hydrogen atom.

$R^2$ represents an alkyl group, an alkenyl group, an aryl group, a halogen atom, a hydroxy group, or an amino group.

The alkyl group that can be represented by $R^2$ may be linear, branched, or cyclic. The number of carbon atoms constituting the alkyl group is not particularly limited, and is, for example, preferably 1 to 10, more preferably 1 to 5, and particularly preferably 1 to 3. Examples of the alkyl group that can be represented by $R^2$ include methyl, ethyl, n-propyl, iso-propyl, n-butyl, tert-butyl, n-octyl, 2-ethylhexyl, n-decyl, and n-hexadecyl.

The alkenyl group that can be represented by $R^2$ may be linear, branched, or cyclic. The number of carbon atoms constituting the alkenyl group is not particularly limited, and is, for example, preferably 2 to 10, more preferably 2 to 6, and particularly preferably 2 to 5. Examples of the alkenyl group that can be represented by $R^2$ include vinyl ($-CH=CH_2$), 2-propenyl ($-CH_2-CH=CH_2$), isopropenyl ($-CH(CH_3)=CH_2$), butenyl, and hexenyl. Of these, a vinyl group or isopropenyl is preferred.

The aryl group that can be represented by $R^2$ includes an aromatic hydrocarbon ring group and an aromatic heterocyclic group, and may be a monocyclic ring or a fused ring. The aromatic hydrocarbon ring group is not particularly limited, but preferably has 6 to 14 carbon atoms. Examples of the aromatic hydrocarbon ring group include phenyl and naphthyl.

The ring-constituting hetero atom constituting the aromatic heterocyclic group is preferably a nitrogen atom, an oxygen atom, or a sulfur atom. For the ring-constituting atoms of the monocyclic aromatic heterocyclic group, a 5-membered ring or a 6-membered ring is preferred. Examples of the aromatic heterocyclic group include a group formed of a nitrogen-containing heterocycle such as a pyrrole ring or a pyridine ring, a furan ring group, a thiophene ring group, and a benzothiazole ring group.

Examples of the halogen atom that can be represented by $R^2$ include a fluorine atom, a chlorine atom, a bromine atom, and an iodine atom.

Examples of the amino group that can be represented by $R^2$ include an unsubstituted amino group ($-NH_2$) and a mono- or di-alkyl- or aryl-amino group substituted with an alkyl group or an aryl group. The alkyl group and the aryl group are not particularly limited, and examples include the above-described alkyl groups and aryl groups that can be represented by $R^2$.

The group that can be represented by $R^2$ is preferably an alkenyl group, and more preferably a vinyl group or isopropenyl.

When k described later is an integer of 1 or more, the position of the benzene ring to which $R^2$ is bonded is not particularly limited, and may be the 2-position (ortho position) or the 3-position (meta position) with respect to the ring-constituting carbon atom to which the ethylenic double bond (vinyl group having $R^1$) is bonded, but is preferably the 3-position.

$R^3$ represents an alkyl group, an alkenyl group, an aryl group, a halogen atom, an amino group, a carboxy group, or a group having a $-SO_3^-M^+$ group, or a group that is a combination of an alkyl group, an alkenyl group, an aryl group, an oxygen atom, a $-SO_3^-M^+$ group, or an arylsulfonylamino group. Note that, when m described later is 0, at least one of n $R^3$'s is a group having a $-SO_3^-M^+$ group.

The alkyl group, the alkenyl group, the aryl group, the halogen atom, and the amino group that can be represented by $R^3$ have the same meanings as the alkyl group, the alkenyl group, the aryl group, the halogen atom, and the amino group that can be represented by $R^2$.

The group having a $-SO_3^-M^+$ group that can be represented by $R^3$ is a group that introduces the $-SO_3^-M^+$ group into the benzene ring in the general formula (I), with a linking group disposed therebetween. The linking group is not particularly limited and may be appropriately selected, but preferred examples include an alkylene group, an alkenylene group, and an arylene group. Examples of these groups include groups in which one hydrogen atom is further removed from each of the alkyl group, the alkenyl group, and the aryl group that can be represented by $R^2$.

The combination group that can be represented by $R^3$ is a group that is an appropriate combination of two or more groups selected from the group consisting of an alkyl group, an alkenyl group, an aryl group, an oxygen atom, a $-SO_3^-M^+$ group, and an arylsulfonylamino group.

The alkyl group, the alkenyl group, and the aryl group that form the combination group respectively have the same meanings as the alkyl group, the alkenyl group, and the aryl group that can be represented by $R^2$. The aryl group constituting the arylsulfonylamino group has the same meaning as the aryl group that can be represented by $R^2$, and is preferably an aromatic hydrocarbon ring group, and more preferably a benzene ring group.

The number of groups combined in the combination group is not particularly limited, but is, for example, preferably 2 to 10, more preferably 2 to 8, still more preferably 2 to 6, and particularly preferably 2 to 4. The groups for the combination are not particularly limited; a combination including an alkenyl group and a $-SO_3^-M^+$ group or an arylsulfonylamino group is preferred, or a combination group that can be represented by $R^4$ described later can alternatively be employed.

The combination group is preferably a combination group of a vinyl group and a $-SO_3^-M^+$ group or a combination group of a vinyl group and a phenylsulfonylamino group (bonded to the benzene ring in the general formula (I) via the nitrogen atom of the phenylsulfonylamino group).

$R^3$ is preferably an alkyl group, an alkenyl group, or the above-described combination group, and more preferably the combination group.

When n described later is an integer of 1 or more, the position of the benzene ring to which $R^3$ is bonded is not particularly limited, and may be the 2-position (ortho position) or the 3-position (meta position) with respect to the ring-constituting carbon atom to which the sulfonylamino group is bonded.

In the general formula (I), $R^4$ represents a hydrogen atom, an alkyl group, an alkenyl group, an aryl group, a halogen atom, an amino group, or a carboxy group, or a combination group of an alkyl group, an alkenyl group, an aryl group, an oxygen atom, a $-SO_3^-M^+$ group, or an arylsulfonylamino group.

The alkyl group, the alkenyl group, the aryl group, the halogen atom, and the amino group that can be represented by $R^4$ respectively have the same meanings as the alkyl group, the alkenyl group, the aryl group, the halogen atom, and the amino group that can be represented by $R^2$.

The alkyl group, the alkenyl group, and the aryl group forming the combination group that can be represented by $R^4$ respectively have the same meanings as the alkyl group, the alkenyl group, and the aryl group that can be represented by $R^2$. The arylsulfonylamino group has the same meaning as the arylsulfonylamino group constituting the combination group that can be represented by $R^3$.

The combination group that can be represented by $R^4$ is a group formed by appropriately combining two or more groups selected from the group consisting of an alkyl group, an alkenyl group, an aryl group, an oxygen atom, a $—SO_3^-M^+$ group, and an arylsulfonylamino group. The number of groups combined is not particularly limited, but is, for example, preferably 2 to 16, more preferably 2 to 12, still more preferably 2 to 8, and particularly preferably 3 to 6. The groups combined are not particularly limited, but a combination including an alkenyl group and an arylsulfonylamino group is preferred, and a combination further including an aryl group and a $—SO_3^-M^+$ group is more preferred. Examples of the combination group include a p-vinyl-substituted phenylsulfonylamino group and a group including a p-vinyl-substituted phenylsulfonylamino group.

Specific examples of the p-vinyl-substituted phenylsulfonylamino group include a "p-vinyl-substituted phenylsulfonylamino group" bonded to the central benzene ring in the chemical formula represented by a general formula (III) or (IV) described later. Examples of the group including a p-vinyl-substituted phenylsulfonylamino group include a group including a p-vinyl-substituted phenylsulfonylamino group and a linking group (for example, $L^A$ or $L^B$ described later), and specific examples thereof include a "p-vinyl-substituted phenylsulfonylamino group including $L^A$ or $L^B$" that is bonded to the second benzene ring from the left in the chemical formula represented by a general formula (V) or (VI) described later.

$R^4$ is preferably a hydrogen atom, an alkyl group, an alkenyl group, or the above-described combination group, and more preferably the above-described combination group.

In the general formula (I), $M^+$ forming the $—SO_3^-M^+$ group represents $H^+$, $Li^+$, $Na^+$, $K^+$, $Cs^+$, or an ammonium salt.

The ammonium salt that can be represented by $M^+$ is not particularly limited and may be $NH_4^+$ or an organic ammonium salt having at least one organic group. Examples of the organic group constituting the organic ammonium salt include an alkyl group and an aryl group, and an alkyl group is preferred. The alkyl group is not particularly limited, but is preferably an alkyl group having 1 to 18 carbon atoms, and more preferably an alkyl group having 1 to 6 carbon atoms. The aryl group is not particularly limited, and examples thereof include the aryl groups that can be represented by $R^2$. The number of organic groups (number of substitutions) in the organic ammonium salt is one or more (secondary to quaternary ammonium salt), but is preferably three (tertiary ammonium salt) or four (quaternary ammonium salt). When two or more organic groups are present, the organic groups may be the same or different. The organic ammonium salt is preferably a tertiary alkyl ammonium salt or a quaternary alkyl ammonium salt.

When m described later is an integer of 1 or more, the position of the benzene ring to which the $—SO_3^-M^+$ group is bonded is not particularly limited, and may be the 2-position (ortho position) or the 3-position (meta position) with respect to the carbon atom to which the sulfonylamino group is bonded, but is preferably the 3-position.

In the compound represented by the general formula (I), $R^1$ to $R^4$ can be appropriately combined, and preferred combinations of $R^1$ to $R^4$ may be combinations of preferred groups that can be represented by $R^1$ to $R^4$ and specifically may be combinations in the Exemplary compounds described later.

In the general formula (I), k is an integer of 0 to 4, preferably an integer of 0 to 2, and more preferably 0 or 1. n is an integer of 0 to 4, preferably an integer of 0 to 2, and more preferably 0 or 1. m is an integer of 0 to 4, preferably an integer of 1 to 3, and more preferably 1 or 2. Note that n and m satisfy $1 \leq n+m \leq 4$ and preferably satisfy $1 \leq n+m \leq 2$.

When k and n are each an integer of 2 or more, a plurality of $R^2$'s and a plurality of $R^3$'s may be the same or different, and may be linked together to form a ring. For example, in Exemplary compound (13) described later, a vinyl group having a $—SO_3^-M^+$ group and a vinyl group that serve as $R^3$'s are bonded to adjacent ring-constituting carbon atoms, and these two vinyl groups are linked together to form a ring fused with the benzene ring (naphthalene ring). When m is an integer of 2 or more, a plurality of $—SO_3^-M^+$ groups may be the same or different.

The compound represented by the general formula (I) may be a monofunctional polymerizable compound or a polyfunctional polymerizable compound. In the present invention, the "monofunctional polymerizable compound" means a compound in which the number of ethylenic double bonds present in the molecular structure is 1, and examples thereof include compounds represented by the formula (I) above or a formula (II) below in which $R^2$ to $R^4$ do not have an ethylenic double bond (alkenyl group). On the other hand, the "polyfunctional polymerizable compound" means a compound in which the number of ethylenic double bonds present in the molecular structure is two or more, and when groups represented by $R^2$ to $R^4$ and the like have ethylenic double bonds, these are included in the determination of the number of functional groups of the compound. Examples thereof include compounds represented by any one of formulas (III) to (VI) described later.

The compound represented by the general formula (I) is preferably a monofunctional polymerizable compound from the viewpoint of water permeability when used in a polymerized film, but is preferably a polyfunctional polymerizable compound from the viewpoint of the effect of improving acid resistance and alkali resistance when formed into a polymer or used in a polymerized film.

The compound represented by the general formula (I) is preferably represented by the following general formula (II):

General formula (II)

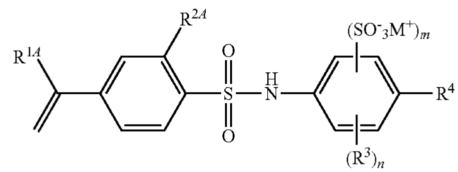

In the general formula (II), $R^{1A}$ represents a hydrogen atom or a methyl group, and is preferably a hydrogen atom. $R^{2A}$ represents a hydrogen atom, $—CH{=}CH_2$, or $—C(CH_3){=}CH_2$, preferably $—CH{=}CH_2$ or $—C(CH_3){=}CH_2$, and more preferably $—CH{=}CH_2$. $R^3$, $R^4$, and $M^+$ have the same meanings and preferred examples as $R^3$, $R^4$, and $M^+$ of the general formula (I). The bonding positions of $R^3$ and the $—SO_3^-M^+$ group in the benzene ring are also the same as those in the general formula (I). Preferred combinations of $R^{1A}$, $R^{2A}$, $R^3$, and $R^4$ are the same as the combinations of $R^1$ to $R^4$ in the general formula (I) except that the groups that can be represented by $R^{1A}$ and $R^{2A}$ are limited as described above.

m is 1 or 2. n is an integer of 0 to 2, and is preferably 0 or 1.

In a preferred embodiment, the compound represented by the general formula (I) is a compound represented by a general formula (III) below. The compound represented by the general formula (III) is a compound in which a p-vinyl-substituted phenylsulfonylamino group among the above-described combination groups is applied as $R^4$ of the general formula (I), is a polyfunctional polymerizable compound, and preferably a bifunctional polymerizable compound or a tetrafunctional polymerizable compound.

General formula (III)

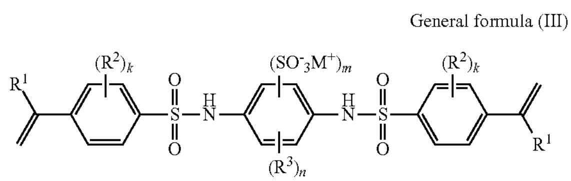

In the general formula (III), $R^1$ to $R^3$, $M^+$, k, m, and n have the same meanings and preferred examples as $R^1$ to $R^3$, $M^+$, k, m, and n in the general formula (I). The bonding positions of $R^2$, $R^3$, and the $—SO_3^-M^+$ group in the benzene rings are also the same as those in the general formula (I). Further, preferred combinations of $R^1$ to $R^3$ are the same as the combinations of $R^1$ to $R^3$ in the general formula (I).

In a more preferred embodiment, the compound represented by the general formula (I) is a compound represented by a general formula (V) below. The compound represented by the general formula (V) is a compound in which a group that is a combination of a p-vinyl-substituted phenylsulfonylamino group and $L^A$ among the above-described combination groups is applied as $R^4$ of the general formula (I). This compound is a polyfunctional polymerizable compound, and is preferably a bifunctional polymerizable compound or a tetrafunctional polymerizable compound.

General formula (V)

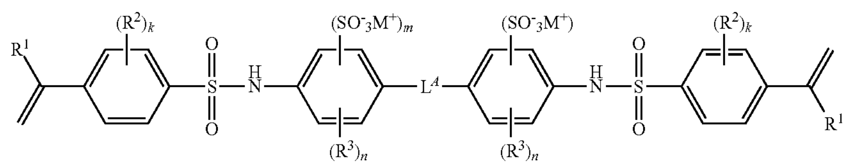

In the general formula (V), $R^1$ to $R^3$, $M^+$, k, m, and n have the same meanings and preferred examples as $R^1$ to $R^3$, k, m, and n in the general formula (I). The bonding positions of $R^2$, $R^3$, and the $—SO_3^-M^+$ group in the benzene rings are also the same as those in the general formula (I). Further, preferred combinations of $R^1$ to $R^3$ are the same as the combinations of $R^1$ to $R^3$ in the general formula (I).

$L^A$ represents a single bond or a divalent linking group. The divalent linking group that can be represented by $L^A$ is not particularly limited and can be appropriately selected, and preferred examples thereof include an oxygen atom (—O— group), an alkylene group, an alkenylene group, and an arylene group. Examples of these groups include groups in which one hydrogen atom has been removed from each of the alkyl group, the alkenyl group, or the aryl group that can be represented by $R^2$ above. Of these, an alkenylene group or an oxygen atom is preferred, an alkenylene group is more preferred, and a —CH═CH— group or a $—CH(CH_3)═CH—$ group is still more preferred. $L^A$ is preferably a single bond, an alkenylene group, or an oxygen atom, and more preferably a single bond or an alkenylene group.

In a preferred embodiment, the compound represented by any one of the general formulas (I) to (III), in particular, the compound represented by the general formula (II), is a compound represented by a general formula (IV) below. The compound represented by the general formula (IV) is a compound in which a p-vinyl-substituted phenylsulfonylamino group among the above-described combination groups is applied as $R^4$ in the general formula (II). This compound is a polyfunctional polymerizable compound, and is preferably a bifunctional polymerizable compound or a tetrafunctional polymerizable compound.

General formula (IV)

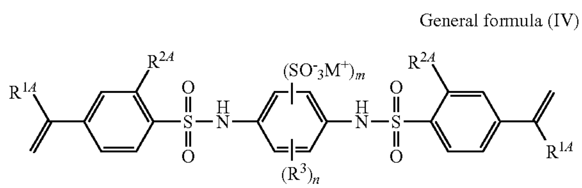

In the general formula (IV), $R^{1A}$, $R^{2A}$, $R^3$, $M^+$, m, and n have the same meanings and preferred examples as the $R^{1A}$, $R^{2A}$, $R^3$, $M^+$, m and n in the general formula (II). The bonding positions of $R^{2A}$, $R^3$, and the $—SO_3^-M^+$ group in the benzene rings are also the same as those in the general formula (II). Further, preferred combinations of $R^{1A}$, $R^{2A}$, and $R^3$ are the same as the combinations of $R^{1A}$, $R^{2A}$, and $R^3$ in the general formula (II).

In a more preferred embodiment, the compound represented by the general formula (I), (II), or (V), in particular, the compound represented by the general formula (II), is a compound represented by a general formula (VI) below. The compound represented by the general formula (VI) is a compound in which a group that is a combination of a p-vinyl-substituted phenylsulfonylamino group and L B among the above-described combination groups is applied as $R^4$ in the general formula (II). This compound is a polyfunctional polymerizable compound, and is preferably a bifunctional polymerizable compound or a tetrafunctional polymerizable compound.

General formula (VI)

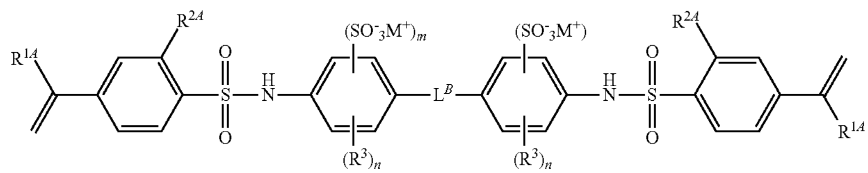

In the general formula (VI), $R^{1A}$, $R^{2A}$, $R^3$, $M^+$, m, and n have the same meanings and preferred examples as $R^{1A}$, $R^{2A}$, $M^+$, m and n in the general formula (II). The bonding positions of $R^{2A}$, $R^3$, and the —$SO_3^-M^+$ group in the benzene rings are also the same as those in the general formula (II). Further, preferred combinations of $R^{1A}$, $R^{2A}$, and $R^3$ are the same as the combinations of $R^{1A}$, $R^{2A}$, and $R^3$ in the general formula (II).

$L^B$ represents a single bond, —CH═CH—, or an oxygen atom, and is preferably a single bond or —CH═CH—.

The compound represented by the general formula (III) or (IV) may have an asymmetric structure with respect to the benzene ring located at the center of each formula (the benzene ring to which the —$SO_3^-M^+$ group can be bonded), but preferably has a symmetric structure. The compound represented by the general formula (V) or (VI) may have an asymmetric structure with respect to the linking group $L^A$ or $L^B$, but preferably has a symmetric structure.

Specific examples of the compound represented by the general formula (I) will be described below; however, the present invention is not limited to these. In the following exemplary compounds, Me represents a methyl group, and Et represents an ethyl group. Note that, in the following exemplary compounds, —CH═CH— groups are described as having trans forms (E isomers) for convenience, but are not limited to these forms, and may have cis forms (Z isomers) or mixtures of the trans form and the cis form.

(1)

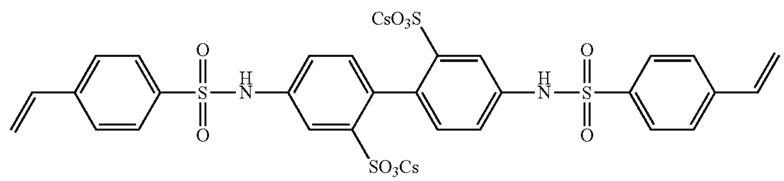

(2)

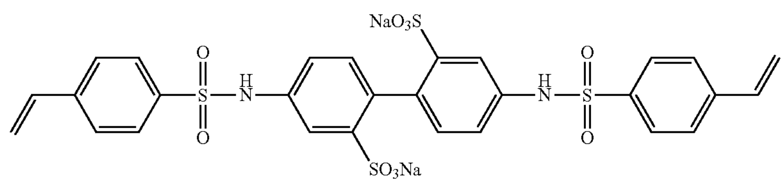

(3)

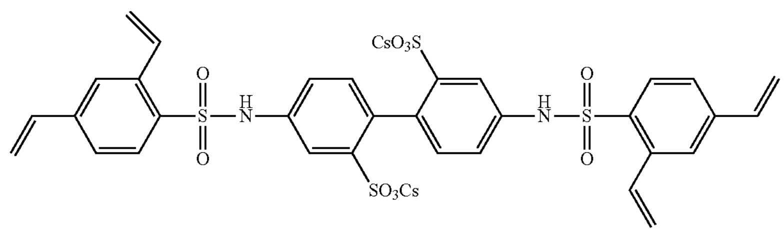

(4)

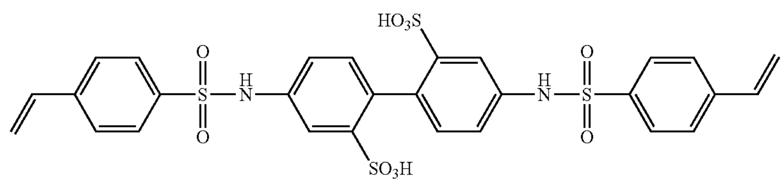

(5)

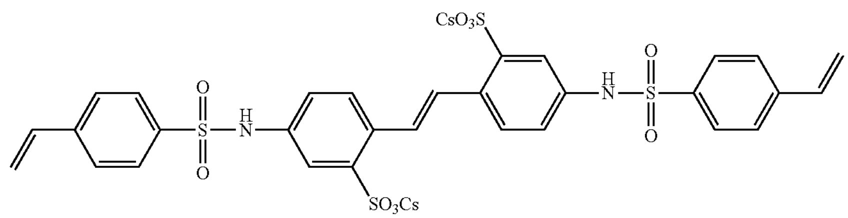

-continued
(6)
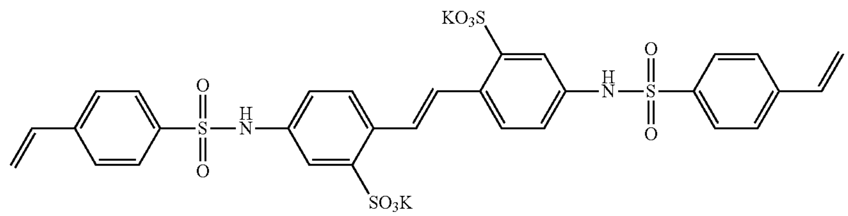
(7)
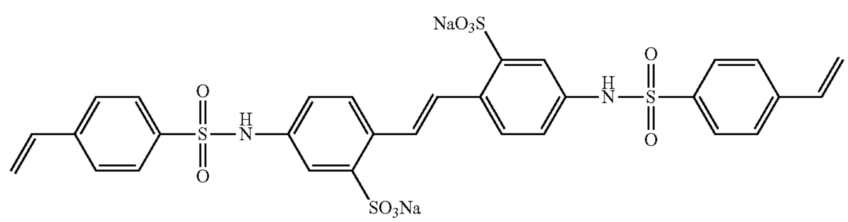
(8)
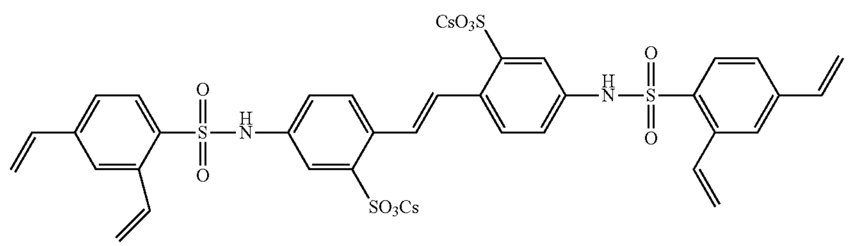
(9)
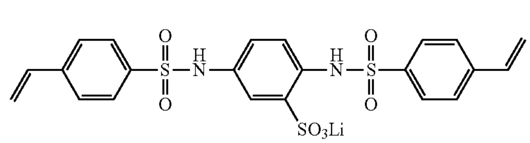
(10)
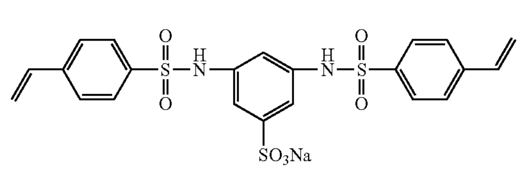
(11)
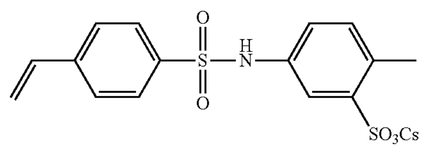
(12)
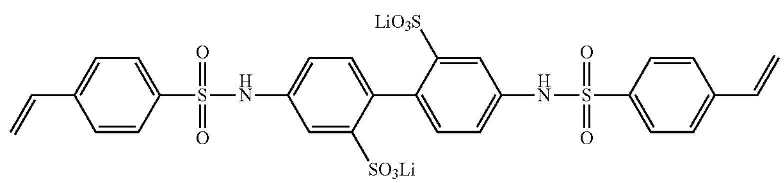
(13)
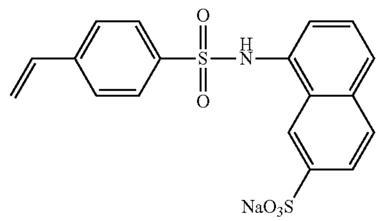
(14)
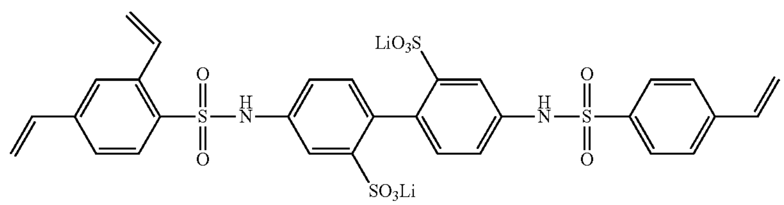

-continued (15)

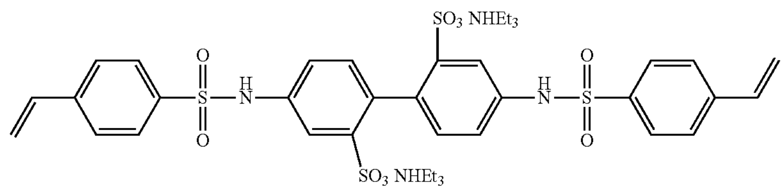

(16)

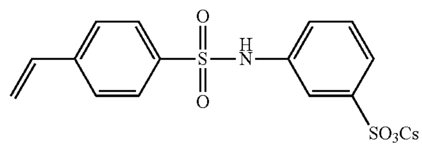

(17)

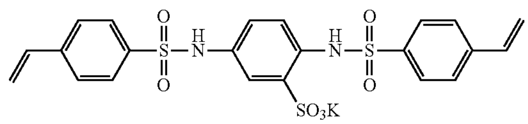

(18)

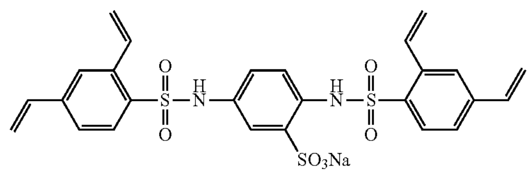

(19)

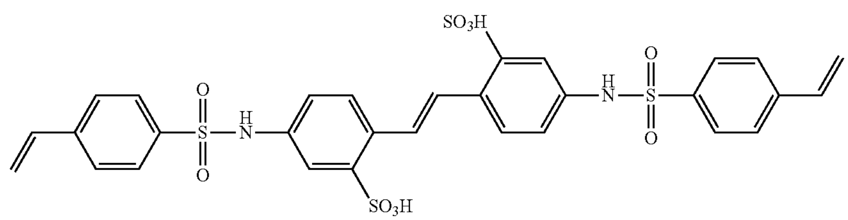

(20)

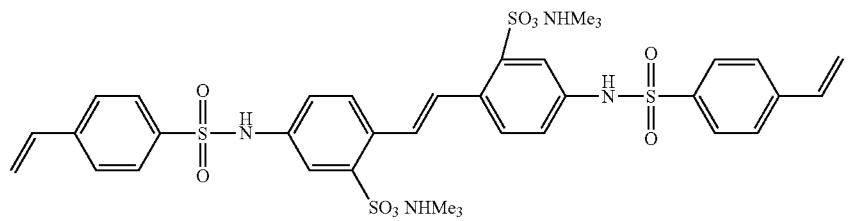

(21)

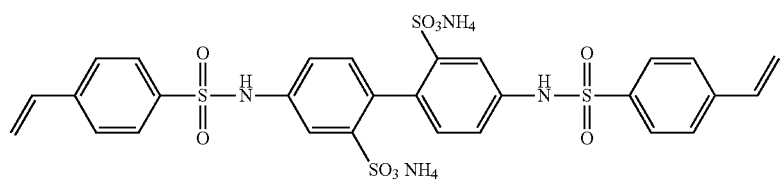

(22)

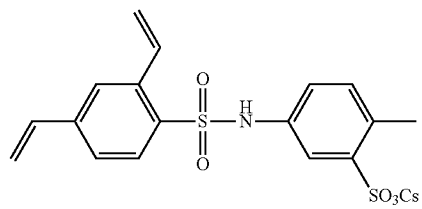

A compound according to the present invention can be synthesized by a publicly known synthesis method or a method in accordance with a synthesis method in Examples described later.

Polymerizable Composition

A polymerizable composition according to the present invention contains (A) at least one compound represented by the general formula (I) as an essential component, and appropriately contains (B) another copolymerizable compound, (C) a polymerization initiator, (D) a co-sensitizer, (E) a polymerization inhibitor, (F) a solvent, (G) an alkali metal compound, or the like.

The compound (A) represented by the general formula (I) (hereinafter, may be referred to as the compound (A)) and contained in the polymerizable composition is not particularly limited, and compounds represented by the above-described general formulas can be appropriately selected. The number of the species of the compound (A) contained in the polymerizable composition is not particularly limited as long as it is 1 or more, but is preferably 2 or more, and can be, for example, 5 or less.

When the polymerizable composition contains a single compound (A), the compound (A) may be a monofunctional polymerizable compound or a polyfunctional polymerizable compound. In a case where the polymerizable composition contains two or more compounds (A), two or more among the compounds represented by the above-described general formulas can be appropriately combined together, but a monofunctional polymerizable compound and a polyfunctional polymerizable compound are preferably combined together.

The total content of the compound (A) in the polymerizable composition is not particularly limited, and is, for example, relative to the total mass of the polymerizable composition, preferably 5 to 95 mass %, more preferably 5 to 60 mass %, still more preferably 10 to 40 mass %, and also preferably 15 to 30 mass %.

When the polymerizable composition contains a monofunctional polymerizable compound and a polyfunctional polymerizable compound among the compounds (A), the content of the monofunctional polymerizable compound is not particularly limited, but, from the viewpoint that water permeability can be improved without considerably impairing the effect of improving acid resistance and alkali resistance when formed into a polymer, the content is, for example, relative to the total mass of the polymerizable composition, preferably more than 0 mass % and 90 mass % or less, more preferably 1 to 20 mass %, and still more preferably 3 to 10 mass %. The content of the polyfunctional polymerizable compound is not particularly limited, but, from the viewpoint that the effect of improving acid resistance and alkali resistance is enhanced while maintaining water permeability when formed into a polymer, the content is, for example, relative to the total mass of the polymerizable composition, preferably more than 0 mass % and 95 mass % or less, more preferably 5 to 60 mass %, and still more preferably 15 to 25 mass %.

(B) Another Copolymerizable Compound

A polymerizable composition according to the present invention may contain, as components for forming a polymer, in addition to the compound (A), another copolymerizable compound that is copolymerizable with the compound (A).

The "another polymerizable compound" is a polymerizable compound different from the compound (A) in terms of chemical structure. This polymerizable compound may be a polyfunctional polymerizable compound, but is preferably a monofunctional polymerizable compound.

Examples of the other polymerizable compound include publicly known polymerizable compounds such as acrylic acid ester compounds, methacrylic acid ester compounds, acrylamide compounds, methacrylamide compounds, vinyl ester compounds, vinyl ether compounds, aromatic vinyl compounds such as styrene compounds, allyl compounds, acrylic acid, methacrylic acid, acrylonitrile, maleic anhydride, and maleimide. By copolymerizing such a polymerizable compound, various properties such as film formability, film strength, hydrophilicity, hydrophobicity, solubility, reactivity, and stability can be improved. Of these, from the viewpoint of, for example, the stability of the polymer functional film to be formed, preferred are compounds having no ester bond, (meth)acrylamide compounds, vinyl ether compounds, aromatic vinyl compounds, N-vinyl compounds (polymerizable monomers having an amide bond), and allyl compounds, and particularly preferred are (meth) acrylamide compounds.

The (meth)acrylamide compounds are preferably a compound represented by the following general formula (B).

General formula (B)

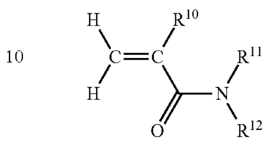

In the general formula (B), $R^{10}$ represents a hydrogen atom or methyl. $R^{11}$ represents a hydrogen atom or a substituted or unsubstituted alkyl group, and $R^{12}$ represents a substituted or unsubstituted alkyl group. $R^{11}$ and $R^{12}$ may be bonded together to form a ring.

$R^{10}$ is preferably a hydrogen atom.

The number of carbon atoms of such an alkyl group in $R^{11}$ and $R^{12}$ is preferably 1 to 18, more preferably 1 to 12, and particularly preferably 1 to 6. The alkyl group is preferably a linear or branched alkyl group, and may have a substituent.

The substituent that the alkyl group may have is not particularly limited, and examples thereof include a hydroxy group, a sulfo group or salts thereof, a carboxy group or salts thereof, a phosphoric acid group or salts thereof, onio groups (such as ammonio, pyridinio, and sulfonio), halogen atoms, alkyl groups, aryl groups, heterocyclic groups, alkoxy groups, aryloxy groups, alkylthio groups, arylthio groups, amino groups (including an amino group, alkylamino groups, arylamino groups, and heterocyclic amino groups), an amide group, a sulfonamide group, a carbamoyl group, a sulfamoyl group, acyl groups, and a cyano group.

In the present invention, in particular, in order to impart a function of the polymerized film, the substituent of the alkyl group is preferably used to impart the function. Thus, among the above-described substituents, preferred are dissociable groups and polar substituents, and particularly preferred are dissociable groups. The dissociable groups are preferably the above-described groups that are a hydroxy group (in particular, a phenolic or enolic hydroxy group), a sulfo group or salts thereof, a carboxy group or salts thereof, and a phosphoric acid group or salts thereof, and more preferably a sulfo group or salts thereof. Preferred examples of the counter cations in the sulfo group, the carboxy group, and the like include organic base ions such as N-methylmorpholinyl and pyridinium and cations of alkali metal atoms such as a lithium cation, a potassium cation, and a sodium cation.

Specific preferred examples of the polymerizable compound represented by the general formula (B) will be described below; however, the present invention is not limited to these.

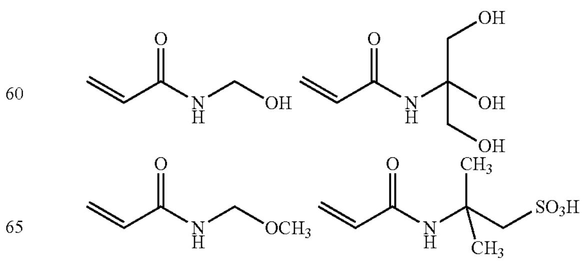

-continued

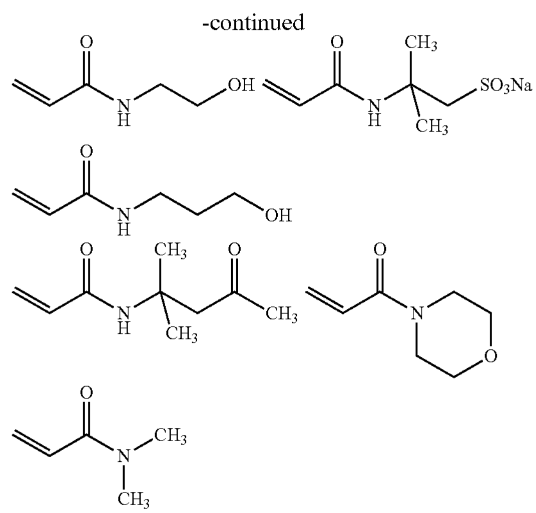

For the other polymerizable compound, which has been described so far, reference can be appropriately made to contents of JP2014-195798A, and the contents as they are incorporated by reference as parts of the descriptions of this Specification.

The other copolymerizable compound is preferably a monofunctional polymerizable compound, and is particularly preferably used in combination with a polyfunctional polymerizable compound represented by any one of the general formulas (III) to (VI).

The total content of the other copolymerizable compounds in the polymerizable composition is not particularly limited, and is, for example, relative to the total mass of the polymerizable composition, preferably 0 to 90 mass %, more preferably 0 to 60 mass %, and still more preferably 3 to 15 mass %.

A polymerizable composition according to the present invention may contain, in addition to the above-described polymerizable compounds, various components such as an additive and a solvent. The polymerizable composition may contain, for each of the various components, one or two or more components. Various components will be briefly described below; for the details of the various components, reference can be appropriately made to the contents described in JP2014-171951A and the contents as they are are incorporated by reference as parts of the descriptions of this Specification.

(C) Polymerization Initiator

A polymerizable composition according to the present invention preferably contains a polymerization initiator.

The polymerization initiator is not particularly limited, but is preferably a photopolymerization initiator capable of polymerizing a polymerizable compound upon irradiation with an energy ray. Examples of such a photopolymerization initiator include aromatic ketones, acylphosphine compounds, aromatic onium salt compounds, organic peroxides, thio compounds, hexaarylbiimidazole compounds, ketoxime ester compounds, borate compounds, azinium compounds, metallocene compounds, active ester compounds, compounds having a carbon-halogen bond, and alkylamine compounds.

In the present invention, a water-soluble polymerization initiator is preferably used. Such a polymerization initiator that is water-soluble means that 0.5 mass % or more of the polymerization initiator dissolves in distilled water at 25° C. The water-soluble photopolymerization initiator more preferably dissolves in distilled water at 25° C. in an amount of 1 mass % or more, and particularly preferably 3 mass % or more.

The content of the polymerization initiator in the polymerizable composition is not particularly limited, and is, for example, relative to the total mass of the polymerizable composition, preferably 0.1 to 10 parts by mass, more preferably 0.1 to 5 parts by mass, and still more preferably 0.3 to 2 parts by mass.

(D) Co-Sensitizer

A polymerizable composition according to the present invention may contain, as a co-sensitizer, a publicly known compound having an action of, for example, further improving sensitivity or suppressing polymerization inhibition due to oxygen. Examples of such a co-sensitizer include amine compounds, thiol and sulfide compounds, amino acid compounds, organometallic compounds, hydrogen donors, sulfur compounds, phosphorus compounds, Si—H, and Ge—H compounds.

The content of the co-sensitizer in the polymerizable composition is not particularly limited, and is, for example, relative to the total mass of the polymerizable composition, preferably 0.01 to 3.00 parts by mass, more preferably 0.05 to 2.00 parts by mass, and still more preferably 0.10 to 1.00 part by mass.

(E) polymerization Inhibitor

A polymerizable composition according to the present invention preferably contains a polymerization inhibitor from the viewpoint of coating stability.

As the polymerization inhibitor, a publicly known polymerization inhibitor can be used, and examples thereof include phenol compounds, hydroquinone compounds, amine compounds, and mercapto compounds.

The content of the polymerization inhibitor in the polymerizable composition is not particularly limited, and is, for example, relative to the total mass of the polymerizable composition, preferably 0.01 to 5 parts by mass, more preferably 0.01 to 1 part by mass, and still more preferably 0.01 to 0.5 parts by mass.

(F) Solvent

A polymerizable composition according to the present invention may contain, as a solvent, at least one of water or an organic solvent. The content of the solvent in the polymerizable composition is not particularly limited, and is ordinarily the balance of the polymerizable composition; for example, the content is, relative to the total mass of the polymerizable composition, preferably 5 to 90 mass %, more preferably 30 to 85 mass %, and still more preferably 50 to 80 mass %.

When the polymerizable composition contains a solvent, the polymerization reaction proceeds uniformly and smoothly. In addition, when a porous support is impregnated with the polymerizable composition, the impregnation can be smoothly achieved.

The organic solvent is preferably an organic solvent having a degree of solubility in water of 5 mass % or more, more preferably an organic solvent freely miscible with water. Thus, a solvent selected from the group consisting of water-soluble solvents is preferred. The water-soluble solvents are not particularly limited, but are preferably alcohol solvents and aprotic polar solvents such as ether solvents, amide solvents, ketone solvents, sulfoxide solvents, sulfone solvents, nitrile solvents, and organic phosphorus solvents.

(G) Alkali Metal Compound

A polymerizable composition according to the present invention may contain an alkali metal compound in order to improve the solubility of the (B) another polymerizable compound, in particular, the compound having a (meth) acrylamide structure. The alkali metal compound is also preferably used for neutralizing the composition or the composition solution mixture.

Preferred examples of the alkali metal compound include hydroxides, chlorides, and nitrates of lithium, sodium, or potassium. Of these, more preferred are lithium compounds and specific examples thereof include lithium hydroxide, lithium chloride, lithium bromide, lithium nitrate, lithium iodide, lithium chlorate, lithium thiocyanate, lithium perchlorate, lithium tetrafluoroborate, lithium hexafluorophosphate, and lithium hexafluoroarsenate. The alkali metal compound may be a hydrate.

The content of the alkali metal compound in the polymerizable compound is not particularly limited, and is, for example, relative to the total mass of the polymerizable composition, preferably 0.1 to 20 parts by mass, more preferably 0.1 to 10 parts by mass, and still more preferably 0.5 to 5 parts by mass.

Other Components etc.

A polymerizable composition according to the present invention may contain various polymer compounds for the purpose of improving properties of the polymerized film. Examples of the polymer compounds include acrylic polymers, polyurethane resins, polyamide resins, polyester resins, epoxy resins, phenol resins, polycarbonate resins, polyvinyl butyral resins, polyvinyl formal resins, shellac, vinyl-based resins, acrylic resins, rubber-based resins, waxes, and other natural resins.

A polymerizable composition according to the present invention may contain a nonionic surfactant, a cationic surfactant, an organic fluoro compound, or the like for the purpose of improving liquid properties of the polymerizable composition.

The polymerizable composition may further contain, for example, a viscosity improver, a surface tension modifier, or a preservative.

A polymerizable composition according to the present invention can be prepared by mixing together the above-described components by an ordinary method.

A polymerizable composition according to the present invention can be suitably used as, for example, a material for forming a polymerized film according to the present invention described later.

Polymer

A polymer according to the present invention has at least one constituent component [A] derived from the compound (A) represented by the general formula (I), and is synthesized by subjecting at least one compound (A) to a polymerization reaction. A polymer according to the present invention exhibits high acid resistance and high alkali resistance due to the compound (A), can be used in a wide range of applications, and is particularly suitable as a polymer constituting a polymerized film.

A polymer according to the present invention preferably has two or more constituent components [A], and also preferably has a constituent component derived from a monofunctional polymerizable compound and a constituent component derived from a polyfunctional polymerizable compound. The constituent component [A] is incorporated into the polymer as at least one of a constituent component derived from a monofunctional polymerizable compound or a constituent component derived from a polyfunctional polymerizable compound, and is preferably incorporated into the polymer as a single constituent component derived from a polyfunctional polymerizable compound. The constituent component [A] may be incorporated, into the polymer, as a constituent component between a constituent component derived from a monofunctional polymerizable compound and a constituent component derived from a polyfunctional polymerizable compound.

The constituent component that may be present in a polymer according to the present invention and that is derived from a compound other than the compound (A) is not particularly limited, and examples thereof include a constituent component [B] derived from the above-described "(B) another copolymerizable compound", and the polymer preferably has the constituent component [B] as a constituent component derived from a monofunctional polymerizable compound.

When a polymer according to the present invention has two or more constituent components, the type of bonding of the constituent components is not particularly limited, and for example, the constituent components may be linked in a block form or in a random form.

Constituent Component Derived from Compound (A)

The constituent component [A] derived from the compound (A) in a polymer according to the present invention is a constituent component obtained by polymerizing a compound represented by any one of the general formulas (I) to (VI), and exhibits high acid resistance and high alkali resistance.

The constituent component [A] is specifically represented by a general formula (IP) below. The constituent component represented by the general formula (IP) is a constituent component derived from the compound represented by the general formula (I); in the general formula (IP), $R^1$ to $R^3$, $M^+$, k, m, and n have the same meanings and preferred examples as $R^1$ to $R^3$, $M^+$, k, m, and n in the general formula (I).

General formula (IP)

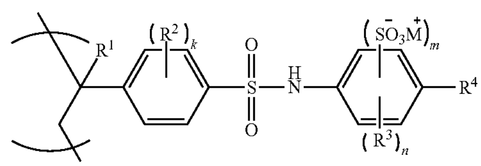

The constituent component represented by the general formula (IP) is preferably represented by a general formula (IIP) below. The constituent component represented by the general formula (IIP) is a constituent component derived from the compound represented by the general formula (II); in the general formula (IIP), $R^{1A}$, $R^{2A}$, $R^3$, $R^4$, $M^+$, m, and n have the same meanings and preferred examples as $R^{1A}$, $R^{2A}$, $R^3$, $R^4$, $M^+$, m, and n in the general formula (II).

General formula (IIP)

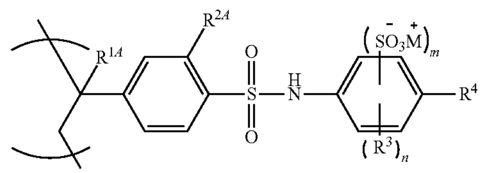

In a preferred embodiment, the constituent component represented by the general formula (IP) is a constituent component represented by a general formula (IIIP) below.

The constituent component represented by the general formula (IIIP) is a constituent component derived from the compound represented by the general formula (III); in the general formula (IIIP), $R^1$ to $R^3$, $M^+$, k, m, and n have the same meanings and preferred examples as $R^1$ to $R^3$, $M^+$, k, m, and n in the general formula (IP).

General formula (IIIP)

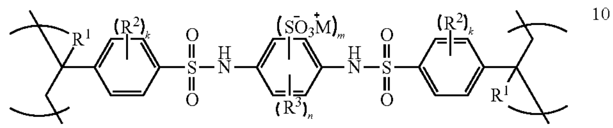

In a more preferred embodiment, the constituent component represented by the general formula (IP) is a constituent component represented by a general formula (VP) below. The constituent component represented by the general formula (VP) is a constituent component derived from the compound represented by the general formula (V); in the general formula (VP), $R^1$ to $R^3$, $M^+$, k, m, and n have the same meanings and preferred examples as $R^1$ to $R^3$, $M^+$, k, m, and n in the general formula (IP).

Gemeral formula (VP)

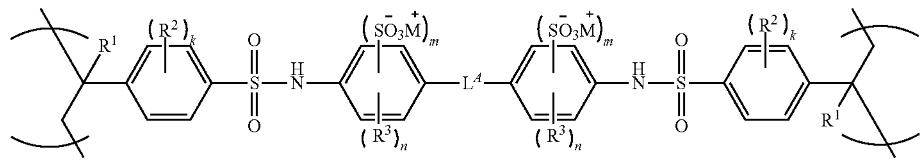

In a preferred embodiment, the constituent component represented by any one of the general formulas (IP) to (IIIP), in particular, the constituent component represented by the general formula (IIP) is a constituent component represented by a general formula (IVP) below. The constituent component represented by the general formula (IVP) is a constituent component derived from the compound represented by the general formula (IV); in the general formula (IVP), $R^{1A}$, $R^{2A}$, $R^3$, $M^+$, m, and n have the same meanings and preferred examples as $R^{1A}$, $R^{2A}$, $R^3$, $M^+$, m, and n in the general formula (IIP).

General formula (IVP)

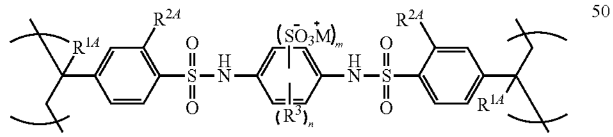

In a more preferred embodiment, the constituent component represented by the general formula (IP), (IIP), or (VP), in particular, the constituent component represented by the general formula (IIP) is a constituent component represented by a general formula (VIP) below. The constituent component represented by the general formula (VIP) is a constituent component derived from the compound represented by the general formula (VI); in the general formula (VIP), $R^{1A}$, $R^{2A}$, $R^3$, $M^+$, m, and n have the same meanings and preferred examples as $R^{1A}$, $R^{2A}$, $R^3$, $M^+$, m, and n in the general formula (TIP).

General formula (VIP)

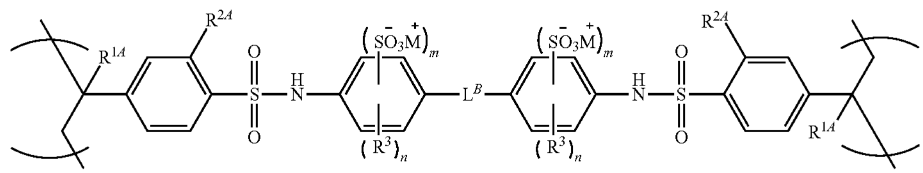

When the constituent components [A] represented by the above-described general formulas have alkenyl groups (ethylenic double bonds) as groups represented by symbols such as $R^2$ to $R^4$, $L^A$, and $L^B$ in the formulas, the alkenyl groups may be polymerized or may not be polymerized.

(B) Constituent Component Derived from Another Copolymerizable Compound

A polymer according to the present invention may have, as a constituent component [B] derived from (B) another copolymerizable compound, a constituent component represented by a formula (PB) below.

General formula (PB)

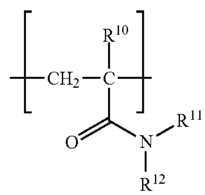

In the general formula (PB), $R^{10}$, $R^{11}$, and $R^{12}$ respectively have the same meanings and preferred examples as $R^{10}$, $R^{11}$, and $R^{12}$ in the general formula (B).

In a polymer according to the present invention, the contents of the constituent component [A] derived from the compound (A) and the constituent component [B] derived from another copolymerizable compound depend on the polymerization reactivity of the compounds and hence are not unconditionally determined, but can be, for example, in the same ranges as in the contents (mass ratios) in the compound in the target polymerizable composition according to the present invention.

A polymer according to the present invention has a constituent component derived from the compound (A) according to the present invention and hence exhibits high acid resistance and high alkali resistance.

The mass-average molecular weight of a polymer according to the present invention is not particularly limited, but in the case where the polymer contains a constituent component derived from a polyfunctional polymerizable compound, three dimensional crosslinking is ordinarily formed, hence the mass-average molecular weight is several hundred thousand or more, and thus cannot be substantially measured. In general, the mass-average molecular weight is regarded as being infinite.

A method for synthesizing a polymer according to the present invention is not particularly limited, and the polymer can be synthesized in accordance with an appropriate method; examples thereof include a method of performing irradiation with an actinic radiation in the production of a polymerized film described later. Note that, for a polymer according to the present invention, the polymer can also be prepared by polymerization performed continuously or simultaneously with the production of a polymerized film in the production of the polymerized film described later.

Polymerized Film

A polymerized film according to the present invention contains at least one polymer according to the present invention.

The content of the polymer in a polymerized film according to the present invention is not particularly limited, but is, for example, in the total mass of the polymerized film, preferably 20 to 98 mass %, and more preferably 50 to 95 mass %. The lower limit value may be set to 70 mass % or may be set to 80 mass %.

A polymerized film according to the present invention (hereinafter, also simply referred to as a film) can be used in a wide range of applications, for example, for ion exchange, selective permeation of ions, proton conduction, fuel cells, or removal of protein aggregates or viruses.

Hereinafter, a preferred embodiment according to the present invention will be described with reference to an example in which a polymerized film according to the present invention has a function of a cation exchange film.

The thickness of the film is not particularly limited, but is, for example, preferably 150 μm or less, more preferably 5 to 150 μm, still more preferably 10 to 130 μm. The thickness of a polymerizable film including a porous support described later is set in such a range, which includes the thickness of the porous support. The term "film thickness" as used herein means a film thickness in a state where the film is impregnated and saturated with a 0.5 M aqueous NaCl solution.

In the film (cation exchange film), the selective permeability for cations such as $Na^+$ is not particularly limited, but is, for example, preferably more than 0.9, more preferably more than 0.93, particularly preferably more than 0.95, and most preferably more than 0.96. The selective permeability of the film preferably has a high value even after the film is treated with an acid and an alkali, and is, for example, preferably 0.85 or more (evaluation grade: C) in EXAMPLES described later.

The water permeability of the film is preferably $14\times10^{-5}$ $mL/m^2/Pa/hr$ or less, more preferably $12\times10^{-5}$ $mL/m^2/Pa/hr$ or less, and most preferably $10\times10^{-5}$ $mL/m^2/Pa/hr$ or less. The water permeability of the film preferably remains the same as the above value and does not considerably decrease even after the film is treated with an acid and an alkali; for example, the amount of change in the water permeability in EXAMPLES described later is preferably less than 30% (evaluation grade: C) or better.

The water absorption of the film is not particularly limited, but is, for example, relative to the mass of the dry film, preferably less than 70%, more preferably less than 50%, and particularly preferably less than 40%.

The ion-exchange capacity of the film is not particularly limited, and is, for example, relative to the total dry mass of the film, the porous support and an optional porous reinforcing material that are continuously in contact with the resultant film, preferably 0.5 meq/g or more, more preferably 0.8 meq/g or more, and particularly preferably 1.2 meq/g or more.

The bursting strength, electrical resistance (film resistance), and swelling ratio in water (ratio of dimensional change due to swelling) of the film are not particularly limited and can be appropriately set. For example, reference can be appropriately made to the contents described in JP2014-171951A and the contents as they are incorporated by reference as parts of the descriptions of this Specification.

The selective permeability can be measured by a method described in Membrane Science, 319, 217 to 218 (2008) and Membranology Experimental Methods, pp. 193 to 195, 1984, written by Nakagaki Masayuki, more specifically, a method that will be described in EXAMPLES.

A polymerized film according to the present invention has a sulfonic group ($SO_3^-$), can be used as, for example, an electrolyte film (ion exchange film), and can exchange cations $Na^+$ in water including a salt such as NaCl. An ideal ion exchange film has low film resistance, low water permeability, and high transport number (cation/anion exchange separation selectivity). In general, the higher the charge density per unit-structure molecular weight, the lower the resistance of the film and the higher the transport number; the higher the crosslinking density, the lower the water permeability. A constituent component derived from a polyfunctional polymerizable compound having a sulfonic group ($—SO_3^-M^+$) is incorporated into the polymer included in a polymerized film according to the present invention, so that the polymerized film has low film resistance, low water permeability, and high transport number.

In addition, a polymerized film according to the present invention includes a polymer having a constituent component derived from the compound represented by the general formula (I). Therefore, the polymerized film exhibits high acid resistance and high alkali resistance due to the compound represented by the general formula (I).

For a polymerized film according to the present invention, in order to provide a film having good mechanical strength, a porous support is preferably used. The porous support is subjected to coating and/or impregnation with and a subsequent curing reaction of the polymerizable composition to thereby function as a support (reinforcing material) for the polymerized film. Such a porous support is not particularly limited, and examples thereof include a synthetic woven fabric, a synthetic nonwoven fabric, a sponge-like film, a film having fine through-holes, and paper. For the details of the porous support, reference can be appropriately made to the contents described in JP2014-171951A, and the contents as they are are incorporated by reference as parts of the descriptions of this Specification.

A polymerized film according to the present invention may contain, in addition to the polymer, various components. Various components that may be contained in the polymerized film are not particularly limited, and are the same as those in the above-described polymerizable composition according to the present invention. Note that, for, for example, components that can be decomposed during polymerization, such as the (C) polymerization initiator and the (E) polymerization inhibitor, and volatile components such as the (F) solvent, residues (decomposition products) thereof may be contained.

A method for producing a polymerized film according to the present invention is not particularly limited. For example, it can be produced by curing a polymerizable composition according to the present invention (polymerizing a compound according to the present invention).

More specifically, it can be formed by applying a polymerizable composition according to the present invention to the surface of a porous support or impregnating the polymerizable composition into the pores of the porous support, and subsequently causing a curing reaction, namely, a polymerization reaction. Alternatively, a polymerized film according to the present invention can be formed by applying a polymerizable composition according to the present invention to the surface of a porous support, impregnating the polymerizable composition into the pores of the porous support, and subsequently causing a curing reaction.

The curing reaction is caused by, for example, a method of subjecting the porous support coated with the polymerizable composition to irradiation with an actinic radiation (for example, an ultraviolet ray or an electron beam) or application of heat. The conditions for forming the polymerized film are not particularly limited, but the temperature is, for example, preferably −30 to 100° C., more preferably −10 to 80° C., and particularly preferably 5 to 60° C.

For the details of the method for producing a polymerized film according to the present invention, reference can be appropriately made to the contents described in JP2014-171951A, and the contents as they are are incorporated by reference as parts of the descriptions of this Specification.

A polymerized film according to the present invention is preferably combined with a porous support to form a composite film, and used in various modules and devices. For example, it can be used in a separation film module or an ion exchange device having a means for ion exchange, desalination, or purification. It can also be suitably used as a fuel cell.

A polymerized film according to the present invention can be suitably used in the form of a module. Examples of the module include a spiral type, a hollow fiber type, a pleated type, a tubular type, a plate & frame type, and a stack type.

A polymerized film according to the present invention is particularly suitable for use in ion exchange; however, other than ion exchange, it can also be suitably used in, for example, proton conductive films for fuel cells or removal of protein or a virus.

EXAMPLES

Hereinafter, the present invention will be described further in detail with reference to Examples; however, the present invention is not construed as being limited thereto. In the following EXAMPLES, "part" and "%" for usage amounts, component formulas, or the like are based on mass unless otherwise specified. In the present invention, "room temperature" means 25° C.

Example 1

1. Synthesis of Compound Represented by General Formula (I)

Synthesis example 1: Synthesis of Exemplary compound (1)

Exemplary compound (1) was synthesized in accordance with the following synthesis scheme.

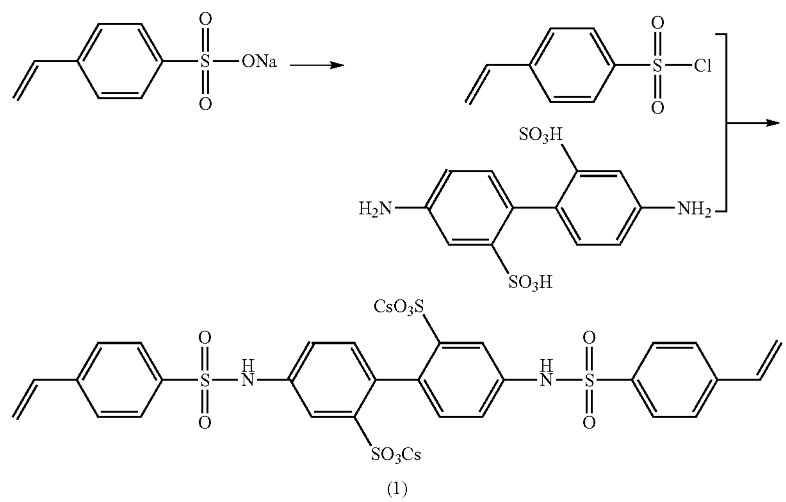

(1)

A solution of 61.9 g of sodium styrene sulfonate and 500 mL of N,N-dimethylformamide was cooled to 0° C. After addition of 0.05 g of 2,6-di-t-butyl-4-methylphenol serving as a polymerization inhibitor, 72.9 mL of thionyl chloride was slowly added dropwise under stirring such that the temperature in the reaction system did not exceed 5° C. After the dropwise addition, the mixture was slowly allowed to warm to room temperature and stirred for 6 hours. After the reaction, the reaction solution was slowly poured into 1 L of ice water, and 700 mL of ethyl acetate was added for extraction. For the aqueous layer, 300 mL of ethyl acetate was used for extraction, the ethyl acetate was combined with the organic layer, and subjected to separation-washing with 500 mL of water repeated three times. The obtained organic layer was dried over magnesium sulfate, and subsequently the solvent was distilled off to thereby obtain 58.6 g of styrenesulfonyl chloride including 8% of ethyl acetate.

The obtained styrenesulfonyl chloride was identified by measurement of a nuclear magnetic resonance spectrum ($^1$H-NMR).

$^1$H-NMR (400 MHz, $CDCL_3$): δ 8.0 (2H), δ 7.6 (2H), δ 6.8 (1H), δ 6.0 (1H), δ 5.5 (1H)

Cesium carbonate (52.1 g) and 19.7 g of 2,2'-benzidinedisulfonic acid (including 30% of water) were dissolved in 400 mL of water, and 150 mL of a toluene solution in which 30 g of styrenesulfonyl chloride was dissolved was added dropwise at room temperature under stirring. After stirring for 6 hours, 2.5 L of acetone was added, and the precipitated solid was obtained by filtration. The obtained solid was dispersed and washed with an acetone-water mixed solution, and subsequently dried to thereby obtain 25.3 g of Exemplary compound (1). The obtained compound was soluble in water.

Figure 2:
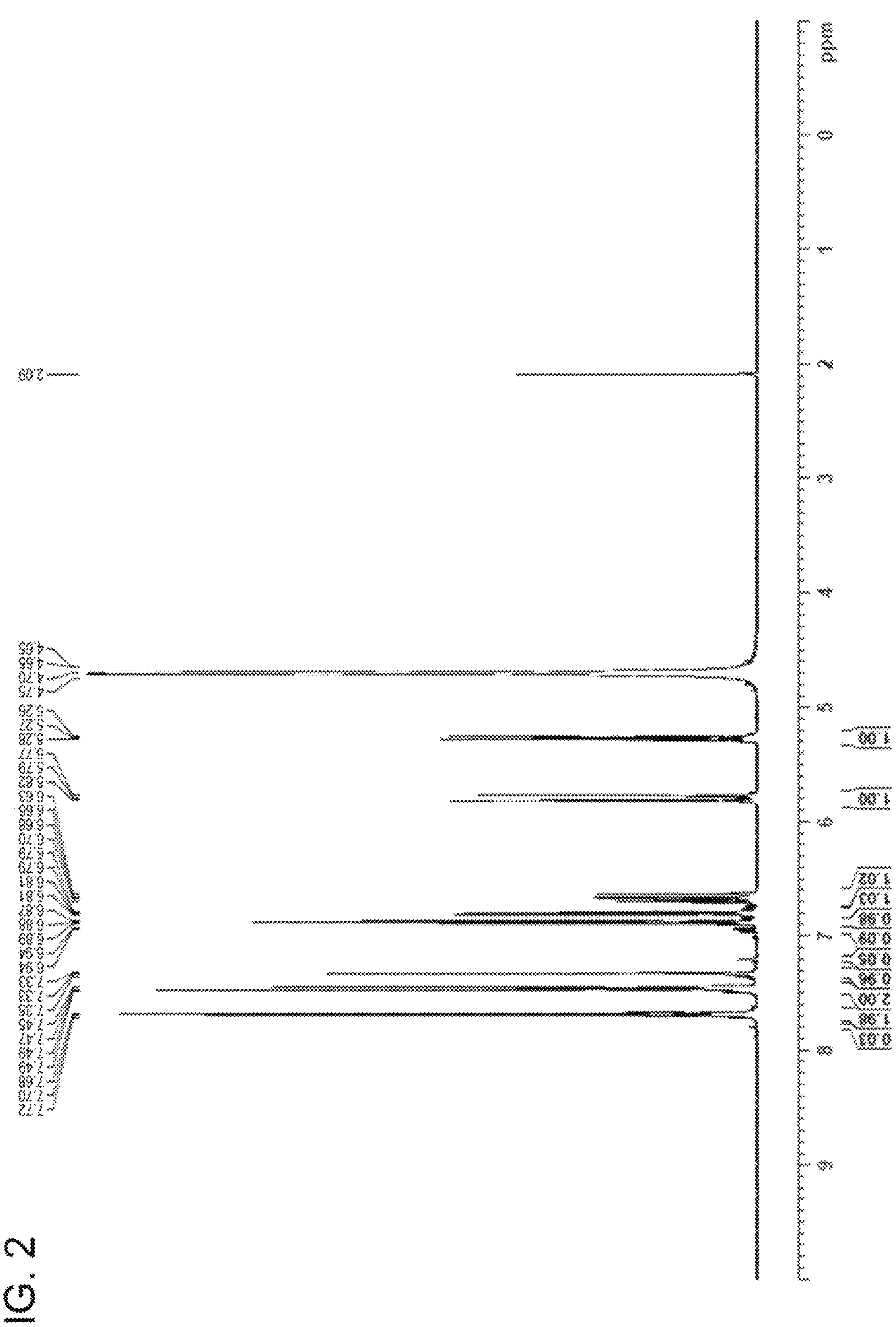
FIG. 2 is an $^1$H-NMR (400 MHz, $D_2O$) chart of Exemplary compound (1) synthesized in EXAMPLES.

The Exemplary compound (1) was identified by measurement of a nuclear magnetic resonance spectrum ($^1$H-NMR). The obtained chart is described in FIG. 2.

$^1$H-NMR (400 MHz, $D_2O$): δ 7.7 (4H), δ 7.5 (4H), δ 7.3 (2H), δ 6.9 (2H), δ 6.8 (2H), δ 6.7 (2H), δ 5.8 (2H), δ 5.3 (2H)

Synthesis Example 2: Synthesis of Exemplary Compound (2)

Exemplary compound (2) was synthesized in accordance with the following synthesis scheme.

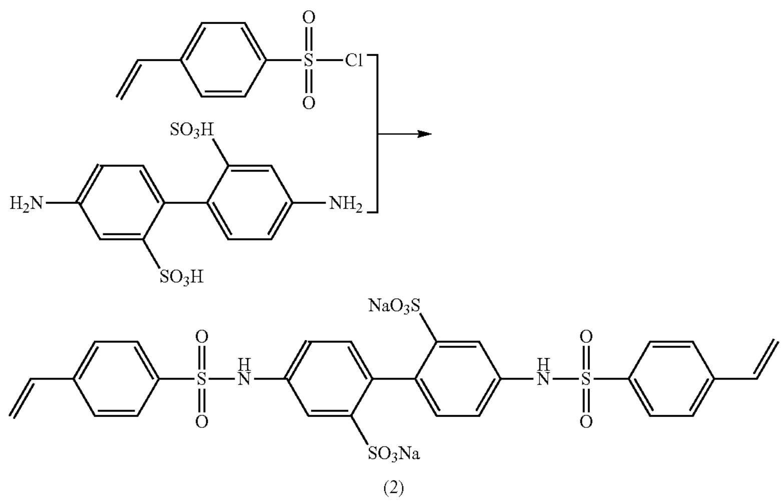

(2)

Sodium carbonate (16.9 g) and 19.7 g of 2,2'-benzidinedisulfonic acid (including 30% of water) were dissolved in 400 mL of water, and 150 mL of a toluene solution in which 30 g styrenesulfonyl chloride was dissolved was added dropwise at room temperature under stirring. After stirring for 6 hours, 2 L of acetone was added, and the precipitated solid was obtained by filtration. The obtained solid was dispersed and washed with an acetone-water mixed solution, and subsequently dried to thereby obtain 25.6 g of Exemplary compound (2). The obtained compound was soluble in water.

Figure 3:
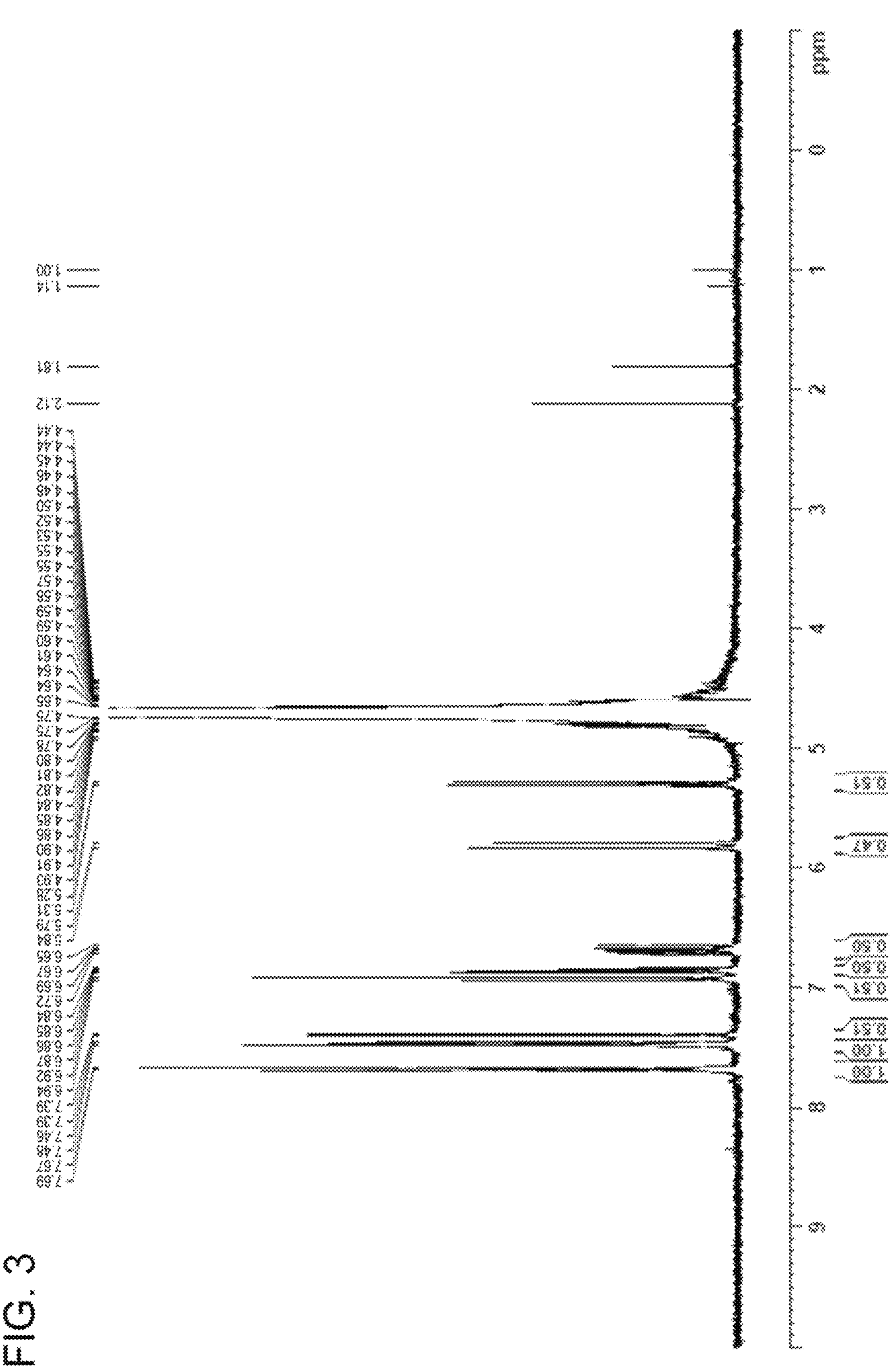
FIG. 3 is an $^1$H-NMR (400 MHz, $D_2O$) chart of Exemplary compound (2) synthesized in EXAMPLES.

The Exemplary compound (2) was identified by measurement of a nuclear magnetic resonance spectrum ($^1$H-NMR). The obtained chart is described in FIG. 3.

$^1$H-NMR (400 MHz, $D_2O$): δ 7.7 (4H), δ 7.5 (4H), δ 7.4 (2H), δ 6.9 (2H), δ 6.8 (2H), δ 6.7 (2H), δ 5.8 (2H), δ 5.3 (2H)

Synthesis Example 3: Synthesis of Exemplary Compound (3)

Exemplary compound (3) was synthesized in accordance with the following synthesis scheme.

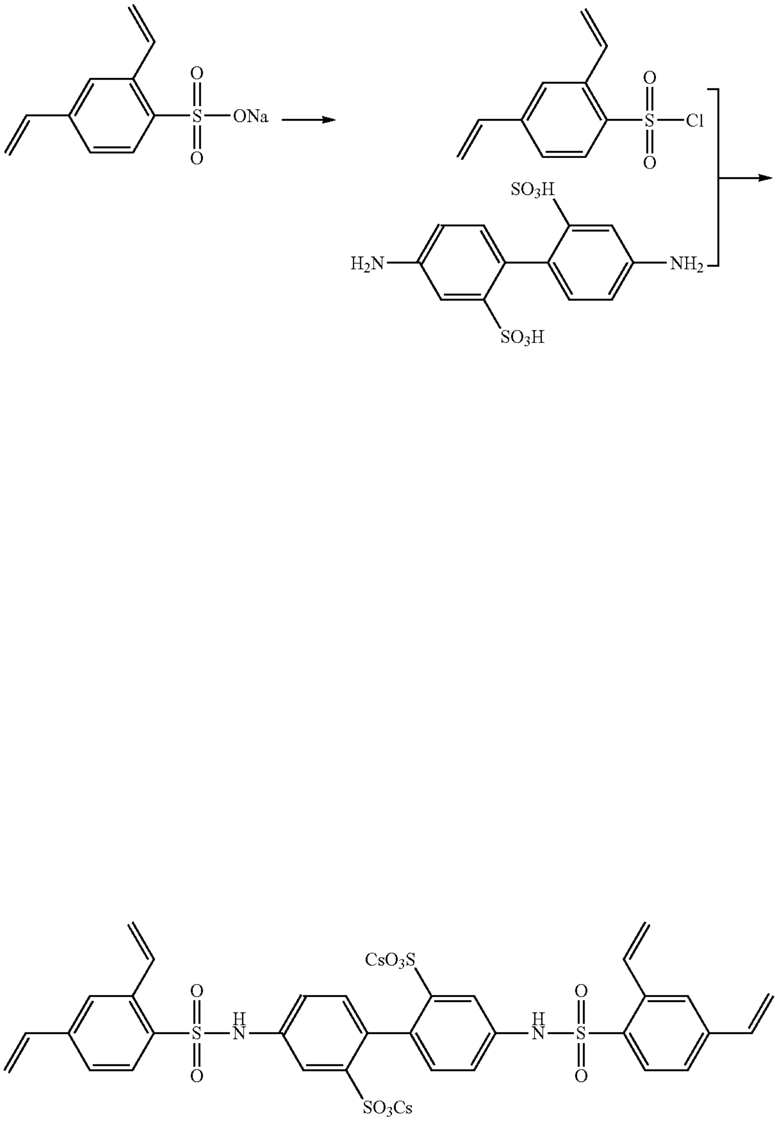

(3)

A solution of 23.2 g of sodium 2,4-divinylbenzenesulfonate and 300 mL of N,N-dimethylformamide was cooled to 0° C. After addition of 0.01 g of 4-hydroxy-2,2,6,6-tetramethylpiperidin 1-oxyl serving as a polymerization inhibitor, 21.9 mL of thionyl chloride was slowly added dropwise under stirring such that the temperature in the reaction system did not exceed 5° C. After the dropwise addition, the mixture was slowly allowed to warm to room temperature and stirred for 6 hours. After the reaction, the reaction solution was slowly poured into 500 mL of ice water, and 500 mL of ethyl acetate was added for extraction. For the aqueous layer, 300 mL of ethyl acetate was used for extraction, the ethyl acetate was combined with the organic layer, and subjected to separation-washing with 500 mL of water repeated three times. After the organic layer was filtered through celite/silica gel, the obtained organic layer was dried over magnesium sulfate and subsequently the solvent was distilled off to thereby obtain 27.2 g of 2,4-divinylbenzenesulfonyl chloride including 31.2% of ethyl acetate.

2,4-Divinylbenzenesulfonyl chloride was identified by measurement of a nuclear magnetic resonance spectrum ($^1$H-NMR).

$^1$H-NMR (400 MHz, $CDCL_3$): δ 8.0 (1H), δ 7.7 (1H), δ 7.6 (1H), δ 7.5 (1H), δ 6.8 (1H), δ 6.0 (1H), δ 5.9 (1H), δ 5.6 (1H), δ 5.6 (1H)

Cesium carbonate (5.2 g) and 1.97 g of 2,2'-benzidinedisulfonic acid (including 30% of water) were dissolved in 40 mL of water, and 14 mL of an ethyl acetate solution in which 4 g of 2,4-divinylbenzenesulfonyl chloride was dissolved was added dropwise at room temperature under stirring. After stirring for 4 hours, 300 mL of acetone was added, and the precipitated solid was obtained by filtration. The obtained solid was dispersed and washed with an acetone-water mixed solution, and subsequently dried to thereby obtain 3.4 g of Exemplary compound (3). The obtained compound was soluble in water.

The Exemplary compound (3) was identified by measurement of a nuclear magnetic resonance spectrum ($^1$H-NMR).

$^1$H-NMR (400 MHz, $D_2O$): δ 7.7 (2H), δ 7.6 (2H), δ 7.5 (2H), δ 7.3 (2H), δ 7.3 (2H), δ 6.8 (2H), δ 6.8 (2H), δ 6.6 (2H), δ 5.8 (2H), δ 5.6 (2H), δ 5.3 (4H)

Synthesis Example 4: Synthesis of Exemplary Compound (5)

Exemplary compound (5) was synthesized in accordance with the following synthesis scheme.

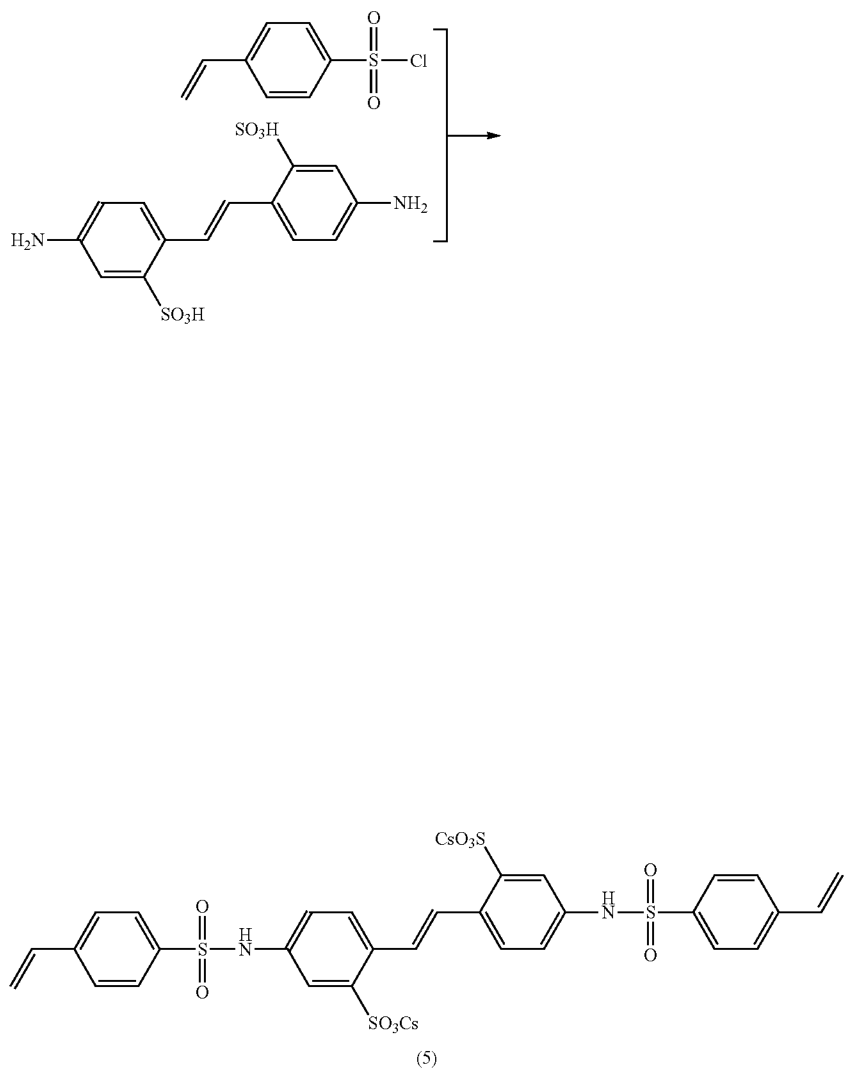

(5)

Cesium carbonate (52.1 g) and 19.7 g of 4,4'-diaminostilbene-2,2'-disulfonic acid were dissolved in 400 mL of water, and 150 mL of a toluene solution in which 30 g of styrenesulfonyl chloride was dissolved was added dropwise at room temperature under stirring. After stirring for 8 hours, 7 L of acetone was added, and the precipitated solid was obtained by filtration. The obtained solid was dispersed and washed with an acetone-water mixed solution, and subsequently dried to thereby obtain 47.1 g of Exemplary compound (5). The obtained compound was soluble in water.

The Exemplary compound (5) was identified by measurement of a nuclear magnetic resonance spectrum ($^1$H-NMR).

$^1$H-NMR (400 MHz, $D_2O$): δ 7.7 (4H), δ 7.5 (4H), δ 7.4 (4H), δ 7.3 (2H), δ 6.9 (2H), δ 6.6 (2H), δ 5.8 (2H), δ 5.2 (2H)

Synthesis Example 5: Synthesis of Exemplary Compound (8)

Exemplary compound (8) was synthesized in accordance with the following synthesis scheme.

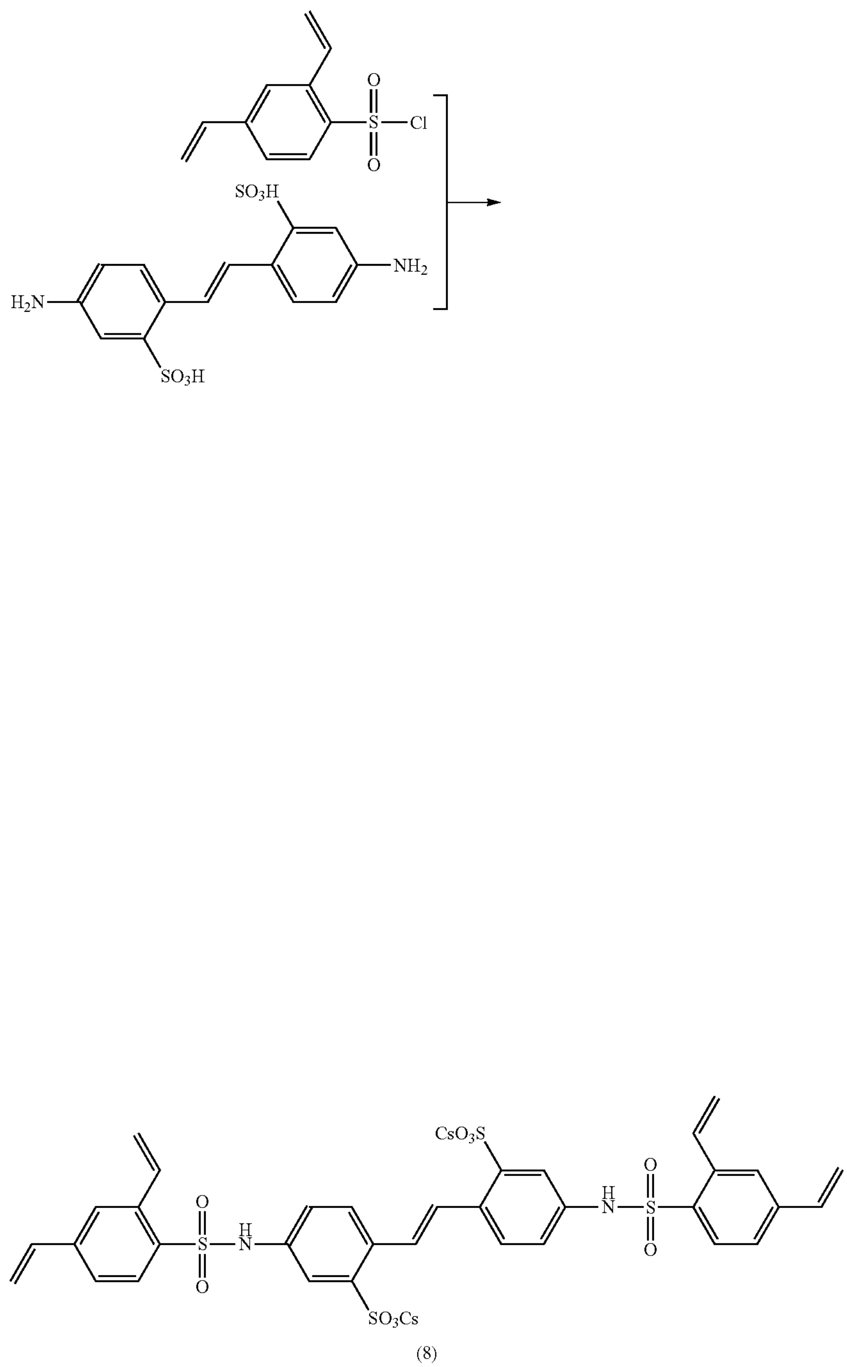

(8)

Cesium carbonate (5.2 g) and 1.66 g of 4,4'-diaminostilbene-2,2'-disulfonic acid were dissolved in 40 mL of water, and 14 mL of an ethyl acetate solution in which 4 g of 2,4-divinylbenzenesulfonyl chloride was dissolved was added dropwise at room temperature under stirring. After stirring for 4 hours, 300 mL of acetone was added, and the precipitated solid was obtained by filtration. The obtained solid was dispersed and washed with an acetone-water mixed solution, and subsequently dried to thereby obtain 3.4 g of Exemplary compound (8). The obtained compound was soluble in water.

Figure 4:
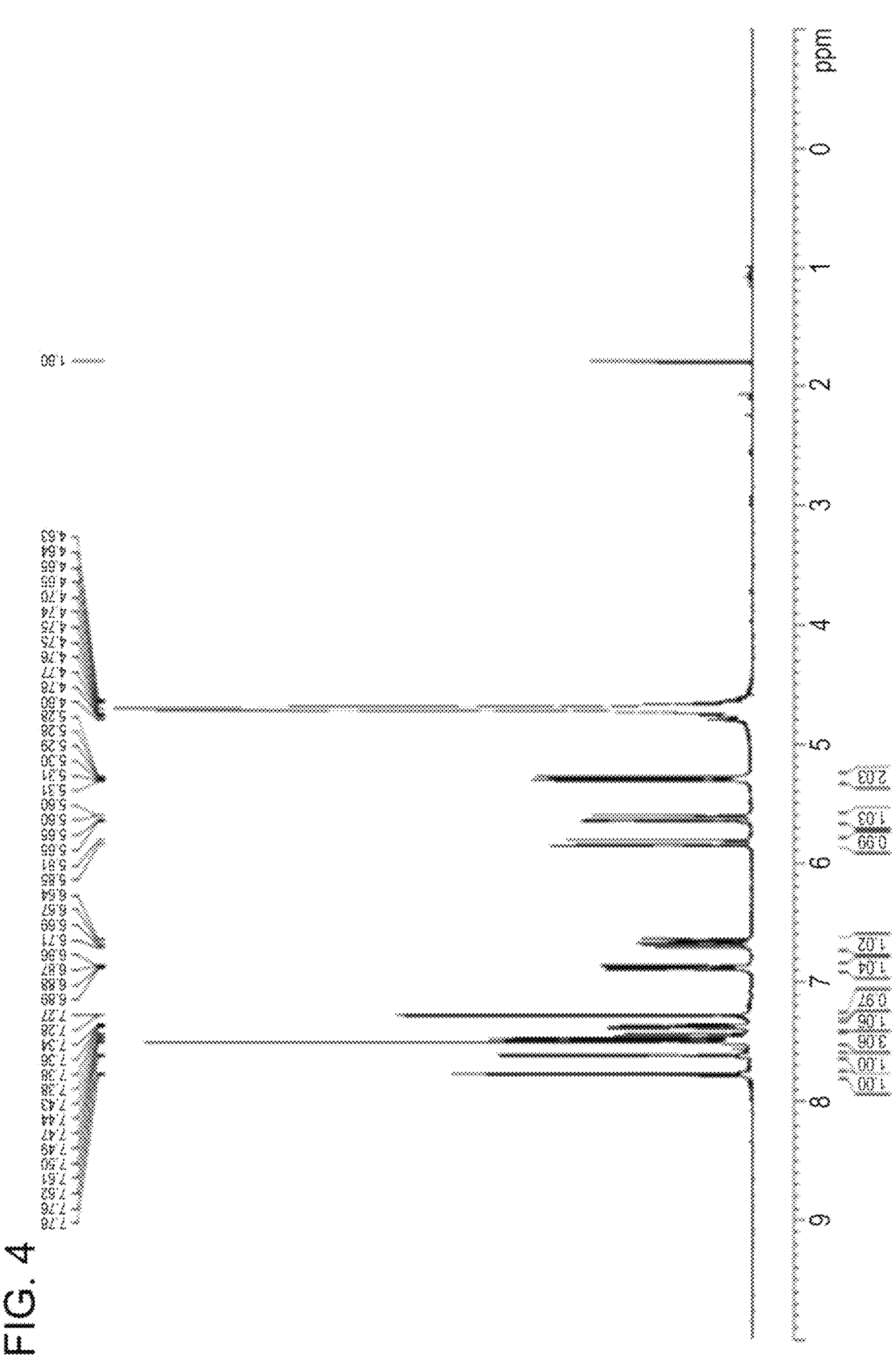
FIG. 4 is an $^1$H-NMR (400 MHz, $D_2O$) chart of Exemplary compound (8) synthesized in EXAMPLES.

The Exemplary compound (8) was identified by measurement of a nuclear magnetic resonance spectrum ($^1$H-NMR). The obtained chart is described in FIG. 4.

$^1$H-NMR (400 MHz, $D_2O$): δ 7.7 (2H), δ 7.6 (2H), δ 7.5 (2H), δ 7.4 (2H), δ 7.4 (2H), δ 7.3 (2H), δ 7.2 (2H), δ 6.8 (2H), δ 6.6 (2H), δ 5.8 (2H), δ 5.6 (2H), δ 5.3 (4H)

Synthesis Example 6: Synthesis of Exemplary Compound (12)

Exemplary compound (12) was synthesized in accordance with the following synthesis scheme.

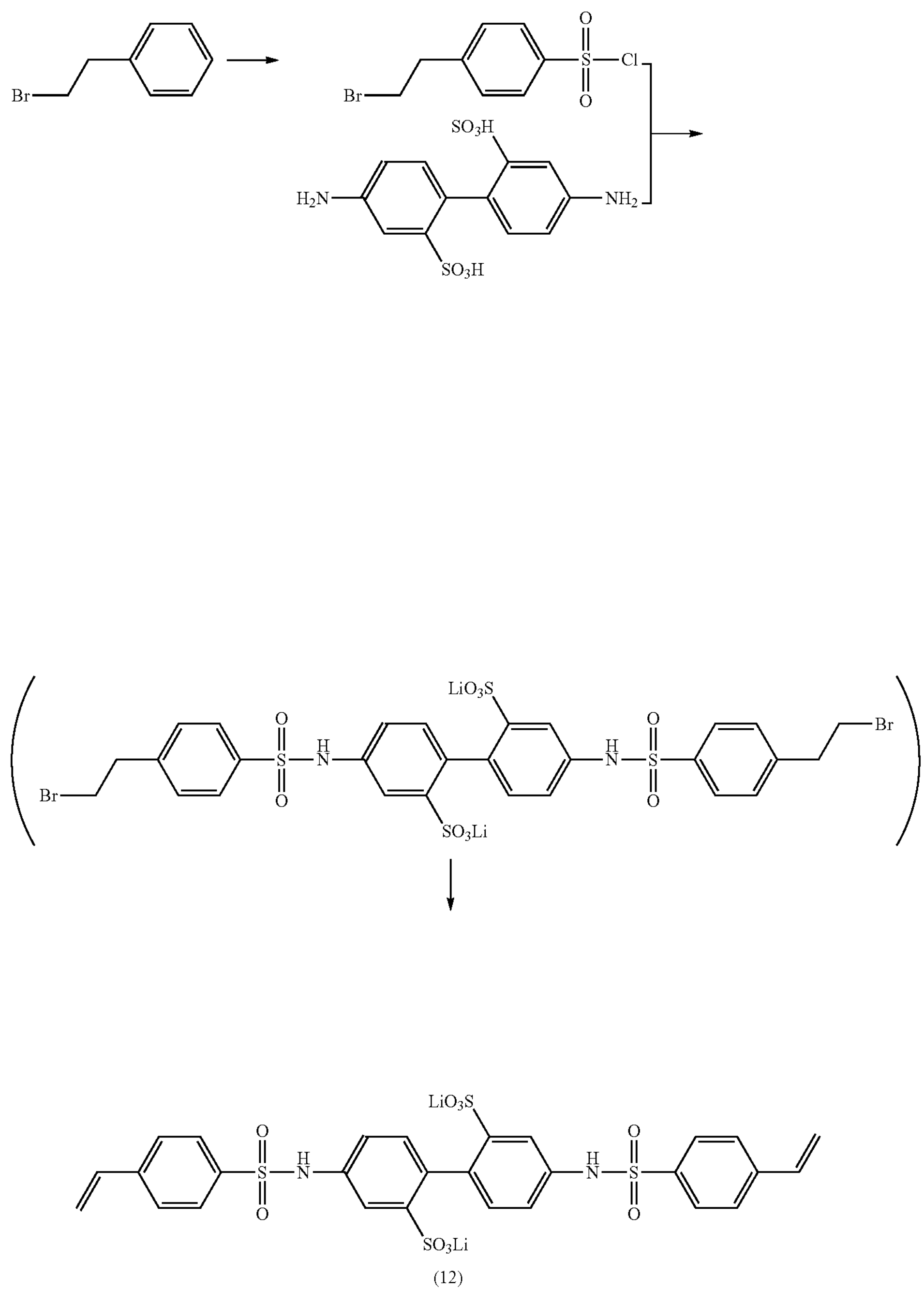

(12)

Lithium hydroxide monohydrate (0.50 g) and 1.97 g of 2,2'-benzidinedisulfonic acid (including 30% of water) were dissolved in 40 mL of water, and 15 mL of a toluene solution of 3.4 g of 4-bromoethylbenzenesulfonyl chloride synthesized in accordance with the method described in JP2019-214608A was added dropwise at room temperature under stirring. After stirring for 6 hours, 0.50 g of lithium hydroxide monohydrate and a small amount of hydroquinone were added, and the mixture was heated to 60° C. and stirred for 3 hours. After cooling to room temperature, 200 mL of acetone was added, and the precipitated solid was obtained by filtration. The obtained solid was dispersed and washed with an acetone-water mixed solution, and subsequently dried to thereby obtain 2.3 g of Exemplary compound (12). The obtained compound was soluble in water.

The Exemplary compound (12) was identified by measurement of a nuclear magnetic resonance spectrum ($^1$H-NMR).

$^1$H-NMR (400 MHz, $D_2O$): δ 7.7 (4H), δ 7.5 (4H), δ 7.3 (2H), δ 6.9 (2H), δ 6.8 (2H), δ 6.7 (2H), δ 5.8 (2H), δ 5.3 (2H)

Synthesis Example 7: Synthesis of Exemplary Compound (16)

Exemplary compound (16) was synthesized in accordance with the following synthesis scheme.

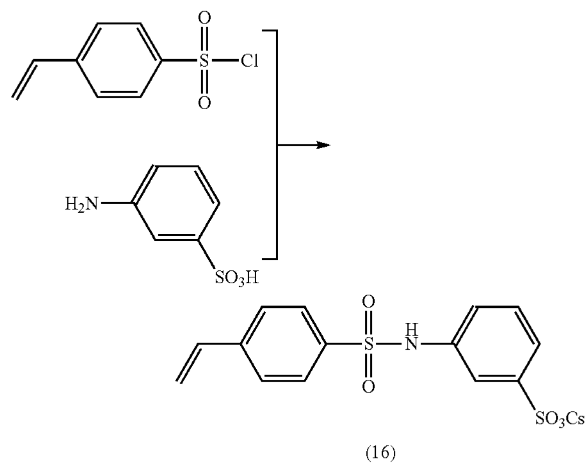

(16)

Cesium carbonate (5.2 g) and 1.39 g of m-aminosulfonic acid were dissolved in 40 mL of water, and 6 mL of an ethyl acetate solution in which 1.5 g of 4-vinylbenzenesulfonyl chloride was dissolved was added dropwise at room temperature under stirring. After stirring for 4 hours, 300 mL of acetone was added to provide two separated layers, and the lower layer was collected. The obtained liquid was purified using a reversed phase column (C18 column) to obtain 2.3 g of Exemplary compound (16). The obtained compound was soluble in water.

The Exemplary compound (16) was identified by measurement of a nuclear magnetic resonance spectrum ($^1$H-NMR).

$^1$-NMR (400 MHz, $D_2O$): δ 7.6 (2H), δ 7.4 (2H), δ 7.2 (1H), δ 7.1 (2H), δ 6.9 (1H), δ 6.6 (1H), δ 5.8 (1H), δ 5.3 (1H)

Synthesis Examples 8 to 10: Synthesis of Exemplary Compounds (9), (11), and (21)

Exemplary compounds (9), (11), and (21) were individually synthesized in accordance with the above-described Synthesis examples and the like.

2. Preparation of Comparative Compounds

As comparative compounds, the following Comparative compounds (1) and (2) were used.

The following Comparative compound (2) was prepared with reference to JP2014-526959A.

Comparative compound (1)

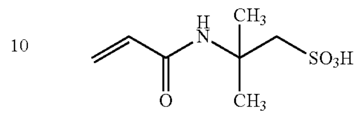

Comparative compound (2)

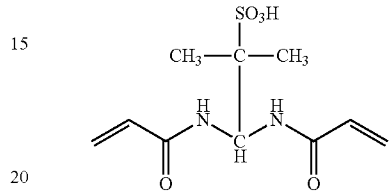

3. Alkali Resistance Test for Compounds Represented by General Formula (I) etc.

Each (5 mg) of Exemplary compounds synthesized in Synthesis examples above was dissolved in 1 mL of heavy water ($D_2O$) and sodium trimethylsilylpropionate (d4) was added thereto as an internal standard substance; subsequently, $^1$H-NMR measurement was performed at room temperature.

Subsequently, a sodium deuteroxide solution was added to the measured sample in such an amount that the concentration became 1 N and mixed; after the lapse of one day, the sample was again subjected to $^1$H-NMR measurement at room temperature. Relative to the area of the peak (0 ppm) of the internal standard substance, the amount of decrease for the peak of each exemplary compound was used to calculate the decomposition ratio of the exemplary compound. As the base for calculation of the decomposition ratio, for Exemplary compound (1), the peak of hydrogen atoms appearing at a chemical shift of δ 7.3 ppm was used; for Exemplary compounds other than Exemplary compound (1), the peaks of hydrogen atoms corresponding to the above-described hydrogen atoms were used.

The alkali resistance (alkali stability) of each exemplary compound was evaluated on the basis of one of the evaluation grades into which the calculated decomposition ratio was included. The results will be described in Table 1.

In this test, the lower the decomposition ratio, the higher the alkali resistance; the evaluation grade "B" or higher are pass grades.

Evaluation Grades

A: less than 10%

B: 10% or more and less than 20%

C. 20% or more

TABLE 1

| No. | Compound No. | Evaluation |
|---|---|---|
| Example 1-1 | Exemplary compound (1) | A |
| Example 1-2 | Exemplary compound (2) | A |
| Example 1-3 | Exemplary compound (3) | A |
| Example 1-4 | Exemplary compound (5) | A |
| Example 1-5 | Exemplary compound (8) | A |
| Example 1-6 | Exemplary compound (9) | A |
| Example 1-7 | Exemplary compound (11) | A |
| Example 1-8 | Exemplary compound (12) | A |

TABLE 1-continued

| No. | Compound No. | Evaluation |
|---|---|---|
| Example 1-9 | Exemplary compound (16) | A |
| Example 1-10 | Exemplary compound (21) | A |
| Comparative example 1-1 | Comparative compound (1) | C |
| Comparative example 1-2 | Comparative compound (2) | C |

Table 1 has demonstrated that Comparative compounds (1) and (2) rapidly undergo hydrolysis reactions in the alkaline environment to exhibit high decomposition ratios, whereas all of the Exemplary compounds belonging to compounds according to the present invention exhibit high alkali resistance even in the alkaline environment.

Example 2

1. Production of Cationic Films 100 to 108

Compositions (coating liquids) 100 to 108 having component formulas in Table 2 below were prepared, and each composition was manually applied to an aluminum plate using a 150 μm wire-wound rod at a rate of about 5 m/min. Subsequently, a nonwoven fabric (FO-2223-10 (trade name), thickness: 100 μm, manufactured by Freudenberg SE) was placed on the coating liquid applied onto the aluminum plate, and the nonwoven fabric was impregnated with the coating liquid. The excess coating liquid not impregnated into the nonwoven fabric was removed using a rod without a wound wire. The temperature of the coating liquid at the time of coating was about 40° C. Subsequently, the coating liquid impregnated into the nonwoven fabric was cured (polymerized) using a UV exposure machine (model: Light Hammer 10, D-bulb, conveyor speed: 15 m/min, 100% intensity, manufactured by Fusion UV Systems Inc.) to thereby produce, on the aluminum plate, a film in which the nonwoven fabric and the cured product (polymer) of the coating liquid were integrated (thickness: 130 μm). Subsequently, the produced film was removed from the aluminum plate and stored in a 0.1 M NaCl solution for at least 12 hours. In this way, the compositions were used to produce Cationic films 100 to 108 of Examples 2-1 to 2-9.

2. Production of Cationic Films c100 and c101 for Comparison

The same procedures as in Example 2-1 were performed except that Compositions c100 and c101 of Comparative examples 2-1 and 2-2 prepared by changing the component formula of the Composition of Example 2-1 to the component formulas in Table 2 below were respectively used with reference to WO2013/011272A to produce Cationic films c100 and c101 of Comparative examples 2-1 and 2-2.

TABLE 2

| | Example 2-1 | Example 2-2 | Example 2-3 | Example 2-4 | Example 2-5 | Example 2-6 | Example 2-7 | Example 2-8 | Example 2-9 | Comparative example 2-1 | Comparative example 2-2 |
|---|---|---|---|---|---|---|---|---|---|---|---|
| Cationic film No. | 100 | 101 | 102 | 103 | 104 | 105 | 106 | 107 | 108 | c100 | c101 |
| Composition No. | 100 | 101 | 102 | 103 | 104 | 105 | 106 | 107 | 108 | c100 | c101 |
| Pure water | 64.15 | 68.00 | 72.64 | 72.64 | 72.64 | 72.64 | 72.64 | 73.20 | 73.20 | 37.10 | 28.20 |
| Genorad 16 | 0.18 | 0.16 | 0.14 | 0.14 | 0.14 | 0.14 | 0.14 | 0.14 | 0.14 | 0.50 | 0.50 |
| $LiOH•H_2O$ | 2.60 | 1.77 | 0.78 | 0.78 | 0.78 | 0.78 | 0.78 | | | | 9.90 |
| Exemplary compound (16) | | | | | | | | 3.88 | 3.88 | | |
| Exemplary compound (1) | 19.25 | 20.40 | 21.79 | | | | | 21.96 | | | |
| Exemplary compound (3) | | | | 21.79 | | | | | | | |
| Exemplary compound (5) | | | | | 21.79 | | | | | | |
| Exemplary compound (8) | | | | | | 20.26 | | | | | |
| Exemplary compound (9) | | | | | | | 21.79 | | 21.96 | | |
| Comparative compound (1) | 12.83 | 8.74 | 3.85 | 3.85 | 3.85 | 5.38 | 3.85 | | | 24.60 | 15.90 |
| Comparative compound (2) | | | | | | | | | | 37.30 | 45.00 |
| Darocur 1173 | 0.50 | 0.46 | 0.40 | 0.40 | 0.40 | 0.40 | 0.40 | 0.41 | 0.41 | 0.50 | 0.50 |
| Tego Glide 432 | 0.50 | 0.46 | 0.40 | 0.40 | 0.40 | 0.40 | 0.40 | 0.41 | 0.41 | | |

In Table 2, the blanks indicate that the contents of the corresponding compounds are 0 mass %.

The compounds in Table 2 are as follows.

Genorad 16 ((trade name)): manufactured by Rahn AG (polymerization initiator)

Darocur 1173 (trade name): 2-hydroxy-2-methylpropiophenone, manufactured by Ciba Specialty Chemicals Tego Glide 432 (trade name): polyether siloxane copolymer, manufactured by Evonik Industries 3. Performance Evaluation of Cationic Films Cationic films 100 to 108, c100, and c101 produced in the above-described manner were evaluated in terms of the following properties.

Selective Permeability (Transport Number) Test

The selective permeability was calculated by measuring the film potential (V) by static film potential measurement. Two electrolytic cells (cells) are separated by the film to be measured. Prior to the measurement, the film was equilibrated in a 0.05 M aqueous NaCl solution for about 16 hours. Subsequently, aqueous NaCl solutions having different concentrations were individually poured into the electrolytic cells on the opposite sides of the film to be measured.

A 0.05 M aqueous NaCl solution (100 mL) was poured into one of the cells. Further, 100 mL of a 0.5 M aqueous NaCl solution was poured into the other cell.

After the temperatures of the aqueous NaCl solutions in the cells were stabilized at 25° C. using a constant-temperature water bath, while both of the solutions were caused to flow to the film surfaces, both electrolytic cells and an Ag/AgCl reference electrode (manufactured by Metrohm AG) were connected via a salt bridge to measure the film potential (V); the transport number t was calculated by the following Formula (A).

Note that the effective area of the film was 1 $cm^2$.

$$t=(a+b)/2b \qquad \text{Formula (A)}$$

The symbols in Formula (A) will be described in detail below.

a: film potential (V)

b: 0.5915 log(f1c1/f2c2) (V)

f1, f2: NaCl activity coefficients of both cells c1, c2: NaCl concentrations of both cells (M)

Water Permeability ($mL/m^2/Pa/hr$) Test

The water permeability of the film was measured using an apparatus having a flow path 10 in FIG. 1. In FIG. 1, Reference sign 1 denotes a film, and Reference signs 3 and 4 respectively denote flow paths of a feed solution (pure water) and a draw solution (3 M NaCl). The arrows denoted by Reference sign 2 indicate the flow of water separated from the feed solution.

The feed solution (400 mL) and 400 mL of the draw solution were brought into contact with each other through the film (film contact area: 18 $cm^2$), and each solution was caused to flow in the direction of the arrow denoted by Reference sign 5 using a peristaltic pump at a flow rate of 0.11 cm/s. The rate at which the water in the feed solution permeated through the film into the draw solution was analyzed by measuring the masses of the feed solution and the draw solution in real time to determine the water permeability.

As a result of the test, Cationic films 100 to 108 produced in Examples 2-1 to 2-9 exhibited selective permeability and water permeability equivalent to those of Cationic films c100 and c101 produced in Comparative examples 2-1 and 2-2, and had sufficient performance as cationic films.

Example 3

1. Production of Acid- and Alkali-Treated Films 200 to 207, c200, and c201

Each of Cationic films 100 to 104, 106 to 108, c100, and c101 produced in Example 2 was immersed in a 4 M aqueous hydrochloric acid solution at 25° C. for 6 hours. Subsequently, the acid-treated cationic film was taken out from the 4 M aqueous hydrochloric acid solution and held in a 0.1 M NaCl solution at 25° C. for at least 12 hours. Subsequently, the cationic film was taken out from the NaCl solution and immersed in a 1 M aqueous sodium hydroxide solution at 25° C. for 6 hours. Subsequently, the alkali-treated cationic film was taken out from the aqueous sodium hydroxide solution and stored (immersed) in a 0.1 M NaCl solution at 25° C. for at least 12 hours. In this way, Acid-treated and alkali-treated cationic films (Acid- and alkali-treated films) 200 to 207, c200, and c201 were produced.

2. Performance Evaluation of Acid- and Alkali-Treated Films

Acid- and alkali-treated films 200 to 207, c200, and c201 produced in the above-described manner were evaluated in terms of selective permeability and water permeability. The results will be described in Table 3.

Selective Permeability (Transport Number) Test

Acid- and alkali-treated films 200 to 207, c200, and c201 were used and measured in terms of selective permeability (transport number) as in "Selective permeability (transport number) test" in Example 2. The selective permeability (transport number) of such an Acid- and alkali-treated film was evaluated on the basis of one of evaluation grades below into which the measured transport number was included.

In this test, the higher the transport number of an Acid- and alkali-treated film, the higher the resistance of the cationic film to the acidic environment and the alkaline environment; the film can maintain the initial high transport number even in these environments.

Evaluation Grades

A: 0.95 or more

B: less than 0.95 and 0.90 or more

C: less than 0.90 and 0.85 or more

D: less than 0.85

Water Permeability ($mL/m^2/Pa/hr$) Test

Acid- and alkali-treated films 200 to 207, c200, and c201 were used and measured in terms of water permeability ($mL/m^2/Pa/hr$) as in "Water permeability ($mL/m^2/Pa/hr$) test" in Example 2.

For the Cationic films 100 to 104 and 106 to 108, c100, and c101 produced in Example 2, the ratios of change in water permeability of the acid- and alkali-treated films were calculated by a formula below. The acid resistance and the alkali resistance of the acid- and alkali-treated films were evaluated on the basis of one of evaluation grades below into which the measured ratio of change was included.

In this test, the lower the ratio of change in water permeability, the higher the acid resistance and alkali resistance of a cationic film produced in Example 2 (the more stable the film to acid and alkali); the acid- and alkali-treated film can maintain high water permeability even in the acidic environment and the alkaline environment.

Amount of change in water permeability (%)=[(Water permeability of Cationic film−Water permeability of Acid- and alkali-treated film)/Water permeability of Cationic film]×100

Evaluation Grades

A: less than 10%

B: 10% or more and less than 20%

C: 20% or more and less than 30%

D: 30% or more

REFERENCE SIGNS LIST

1 film

2 arrow indicating permeation of water in feed solution through film into draw solution

3 flow path of feed solution

4 flow path of draw solution

5 direction of travel of liquid

10 flow path of water permeability measurement apparatus

TABLE 3

| | Example 3-1 | Example 3-2 | Example 3-3 | Example 3-4 | Example 3-5 | Example 3-6 | Example 3-7 | Example 3-8 | Comparative example 3-1 | Comparative example 3-2 |
|---|---|---|---|---|---|---|---|---|---|---|
| Acid- and alkali-treated film No. | 200 | 201 | 202 | 203 | 204 | 205 | 206 | 207 | c200 | c201 |
| Employed Cationic film No. | 100 | 101 | 102 | 103 | 104 | 106 | 107 | 108 | c100 | c101 |
| Selective permeability (transport number) test | B | B | A | A | A | B | A | A | D | D |
| Water permeability test | B | B | A | A | A | B | A | A | D | D |

As described in Table 3, when Cationic films c100 and c101 produced in Comparative examples 3-1 and 3-2 were subjected to the acid treatment and the alkali treatment (turned into Alkali-treated films c200 and c201), the selective permeability considerably decreased and the water permeability considerably increased. This is inferentially because the polymers constituting the cationic films underwent a hydrolysis reaction in the acid treatment or alkali treatment.

In contrast, Cationic films 100 to 104 and 106 to 108 produced in Examples 2-1 to 2-5 and 2-7 to 2-9, even when subjected to the acid treatment and the alkali treatment (even turned into Alkali-treated films 200 to 207), each underwent a small amount of change in water permeability while suppressing decrease in selective permeability, and had high acid resistance and high alkali resistance. This is inferentially because polymers according to the present invention constituting Cationic films 100 to 104 and 106 to 108 contain a constituent component derived from at least one compound according to the present invention, are less likely to undergo a hydrolysis reaction in the acid treatment or the alkali treatment, and the state before the treatments (the chemical structures of the polymers) can be maintained. In particular, it has been demonstrated that, when a compound according to the present invention has a constituent component derived from a polyfunctional polymerizable compound and the content of this constituent component is increased relative to the constituent component derived from a monofunctional polymerizable compound, both of higher selective permeability and higher water permeability can be achieved.

The present invention has been described together with embodiments thereof; however, we do not intend to limit our invention in any minor portion of the descriptions unless otherwise specified; we believe that the invention should be construed broadly without departing from the spirit and scope of the invention described in the attached claims.

What is claimed is:

1. A compound represented by a general formula (I) below,

General formula (I)

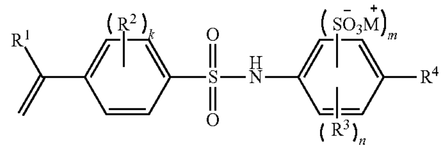

in the general formula (I), $R^1$ represents a hydrogen atom or a lower alkyl group, $R^2$ represents an alkyl group, an alkenyl group, an aryl group, a halogen atom, a hydroxy group, or an amino group, $R^3$ represents an alkyl group, an alkenyl group, an aryl group, a halogen atom, an amino group, a carboxy group, or a group having a $—SO_3^-M^+$ group, or a group that is a combination of an alkyl group, an alkenyl group, an aryl group, an oxygen atom, a $—SO_3^-M^+$ group, or an arylsulfonylamino group, $R^4$ represents a hydrogen atom, an alkyl group, an alkenyl group, an aryl group, a halogen atom, an amino group, or a carboxy group, or a group that is a combination of an alkyl group, an alkenyl group, an aryl group, an oxygen atom, a $—SO_3^-M^+$ group, or an arylsulfonylamino group, $M^+$ represents $H^+$, $Li^+$, $Na^+$, $K^+$, $Cs^+$, or an ammonium salt, k is an integer of 0 to 4, and when k is an integer of 2 or more, a plurality of $R^2$'s may be the same or different, and may be linked together to form a ring, n is an integer of 0 to 4, and when n is an integer of 2 or more, a plurality of $R^3$'s may be the same or different, and may be linked together to form a ring, m is an integer of 0 to 4, and when m is an integer of 2 or more, a plurality of $—SO_3^-M^+$ groups may be the same or different, with the proviso that n and m satisfy $1 \leq n+m \leq 4$, and when m is 0, at least one of $R^3$ is a group having a $—SO_3^-M^+$ group.

2. The compound according to claim 1, wherein the compound represented by the general formula (I) is represented by a general formula (II) below:

General formula (II)

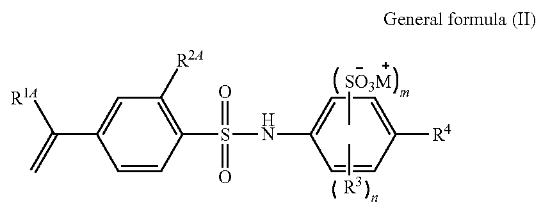

in the general formula (II), $R^{1A}$ represents a hydrogen atom or a methyl group, $R^{2A}$ represents a hydrogen atom, $—CH{=}CH_2$, or $—C(CH_3){=}CH_2$, $R^3$, $R^4$, and $M^+$ have the same meanings as $R^3$, $R^4$, and $M^+$ of the general formula (I), m is 1 or 2, and n is an integer of 0 to 2.

3. The compound according to claim 1, wherein the compound represented by the general formula (I) is represented by a general formula (III) below:

General formula (III)

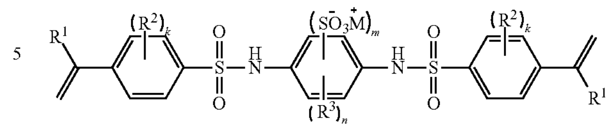

in the general formula (III), $R^1$ to $R^3$, $M^+$, k, m, and n have the same meanings as $R^1$ to $R^3$, $M^+$, k, m, and n in the general formula (I).

4. The compound according to claim 2, wherein the compound represented by the general formula (II) is represented by a general formula (IV) below:

General formula (IV)

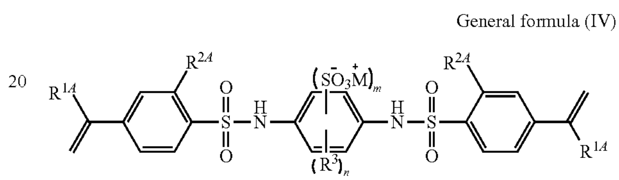

in the general formula (IV), $R^{1A}$, $R^{2A}$, $R^3$, $M^+$, m, and n have the same meanings as the $R^{1A}$, $R^{2A}$, $R^3$, $M^+$, m, and n of the general formula (II).

5. The compound according to claim 1, wherein the compound represented by the general formula (I) is represented by a general formula (V) below:

General formula (V)

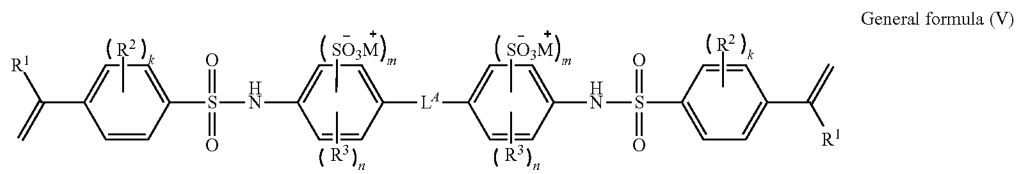

in the general formula (V), $R^1$ to $R^3$, $M^+$, k, m, and n have the same meanings as $R^1$ to $R^3$, $M^+$, k, m, and n in the general formula (I), and $L^A$ represents a single bond or a divalent linking group.

6. The compound according to claim 2, wherein the compound represented by the general formula (II) is represented by a general formula (VI) below:

General formula (VI)

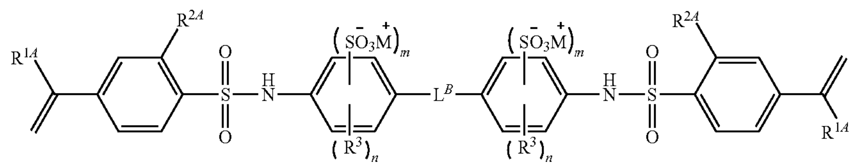

in the general formula (VI), $R^{1A}$, $R^{2A}$, $R^3$, $M^+$, m, and n have the same meanings as the $R^{1A}$, $R^{2A}$, $R^3$, $M^+$, m, and n of the general formula (II), and $L^B$ represents a single bond, —CH═CH—, or an oxygen atom.

7. A polymerizable composition comprising the compound according to claim 1.

8. A polymer comprising a constituent component derived from the compound according to claim 1.

9. A polymerized film comprising the polymer according to claim 8.

* * * * *